(12) United States Patent
Ecker et al.

(10) Patent No.: US 7,220,587 B2
(45) Date of Patent: May 22, 2007

(54) ETHYLENE INSENSITIVE PLANTS

(75) Inventors: Joseph R. Ecker, Carlsbad, CA (US);
Ramlah Nehring, La Jolla, CA (US);
Robert B. McGrath, Philadelphia, PA (US)

(73) Assignees: The Salk Institute for Biological Studies, La Jolla, CA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/152,569

(22) Filed: Jun. 13, 2005

(65) Prior Publication Data

US 2006/0005278 A1    Jan. 5, 2006

Related U.S. Application Data

(62) Division of application No. 10/144,156, filed on May 10, 2002, now abandoned.

(60) Provisional application No. 60/290,303, filed on May 10, 2001.

(51) Int. Cl.
| | |
|---|---|
| A01H 5/00 | (2006.01) |
| C12N 15/82 | (2006.01) |
| C12N 15/87 | (2006.01) |
| C12N 5/14 | (2006.01) |
| C07H 21/00 | (2006.01) |

(52) U.S. Cl. .................. 435/468; 435/320.1; 435/419; 536/23.6; 800/283

(58) Field of Classification Search ..................... None
See application file for complete search history.

(56) References Cited

U.S. PATENT DOCUMENTS

2003/0166197 A1    9/2003    Ecker et al.

FOREIGN PATENT DOCUMENTS

| WO | WO-95/01439 A2 | 1/1995 |
| WO | WO-95/01439 A3 | 1/1995 |
| WO | WO-02/090540 A1 | 11/2002 |

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Quetier et al. (NCBI, GenBank, Sequence Accession No. AL049659, pp. 1-40, Published Apr. 20, 1999).*
Maniatis et al. (Cold Spring Harbor Laboratory, Chapter 12, pp. 404-421, New York, 1982).*
Alonso, J.M. et al. (Jun. 25, 1999). "EIN2, A Bifunctional Transducer of Ethylene and Stress Responses in Arabidopsis," *Science* 284:2148-2152.
Branch et al. (Feb. 1998). *TIBS* 23:45-50.
Database GenBank on STN, Accession No. AL049659, Hoisne, N. et al. *Arabidopsis thaliana* DNA Chromosome 3, BAC clone T29H11, (GBN), Apr. 19, 2000.
Database GenBank on STN, Accesion No. CAB41155, Choisne, N. et al. (GBN), Apr. 19, 2000.
Gordon-Kamm, W. et al. (Jul. 1990). *The Plant Cell* 2:603-618.
Hackett, R.M. (Nov. 2000). "Antisense Inhibition of the Nr Gene Restores Normal Ripening to the Tomato Never-ripe Mutant, Consistent with the Ethylene Receptor Inhibition Model," *Plant Physiology* 124:1079-1085.
International Search Report, dated Aug. 4, 2002, from International Application No. PCT/US02/15049.
Knoester, M. et al. (Feb. 1998). "Ethylene-insensitive Tobacco Lacks Nonhost Resistance Against Soil-Borne Fungi," *PNAS* 95:1933-1937.
Roman, G. et al. (1995). "Genetic Analysis of a Seedling Stress Response to Ethylene in *Arabidopsis*," *Phil Trans. R. Soc. Lond. B* 350:75-81.
Roman, G. et al. (Mar. 1995). "Genetic Analysis of Ethylene Signal Transduction in *Arabidopsis thaliana*: Five Novel Mutant Loci Integrated into a Stree Response Pathway," *Genetics* 139:1393-1409.
Waterhouse, P. et al. (Nov. 1999). *Trends in Plant Sciences* 4(11):452-457.

\* cited by examiner

*Primary Examiner*—Phuong Bui
*Assistant Examiner*—Vinod Kumar
(74) *Attorney, Agent, or Firm*—Morrison & Foerster LLP

(57) ABSTRACT

Nucleic acid and polypeptide sequences are described which relate to an EIN6 gene, a gene involved in the plant ethylene response. Plant transformation vectors and transgenic plants are described which display an altered ethylene-dependent phenotype due to altered expression of EIN6 in transformed plants.

9 Claims, 9 Drawing Sheets

FIGURE 2

```
-1241  atggtcggggaatcccattggaaagtgagtggatactacacattttagttttatggcttggagtccagaacctcc
-1166  gcatgtttctaaagctatatattgatttttgttttggttgccataggtaccggggaaagaggatgaggatcgac
-1091  tattttctggtctctgaacaactcaaagaccgtatagtttcttgtaagatgcacggtcgtgggatagaacttgaa
-1016  ggtgccatagataaacctgttcatcacacagattcatagaagattattattagctcttttttgcaacaatttggtt
-941   cttgatttgtttcaggtttccatgggagtgatcattgtccggttacactcgagctttcgaagccatcttcagaaa
-866   tggaacagaaccaggtgtcaaactaaaatcatcttcttctgtattagaacataaggccttcttaggaacaagcca
-791   aagcttattttatcagagaatttaatttttactttgccgagagatgcattgaagatttgattgaggttattgaga
-716   cacttatttagccttgttactctgatgaactctcaaatgtacttataattattgttgtgcttatcttaatatgtt
-641   ttattttcctaagaaatgttgatattttaattgtgaatcttcttcatttaattattttatttattaacttttg
-566   agtcatttctaaagatttagagcttttgttggtgtattttaagcatattataccctttgctttattgtcttagtc
-491   agtaggtagaggcaacattcgttaaaccaatggctcattcaaattctttttttgggctcattcatattcataaa
-416   aatcaaatttggattcagcataacaaacacaataataaatgtagacatttatatcatacattaatttctactaat
-341   ttcatgaactaccaaagactaaaaatgtttaatgagaaatatcttttttaaaaccatcaaaaattttactcttaa
-266   aattgggatttatgtttggttttaaaaaggagtttttgaatgtgcaaacggatttacagagaggacaacaacaaa
-191   tgtgtgttagaaatggcagaatcgtaaataataagaaaatcatacccttttaaaaaccatttctctctctaacta
-116   agtgttctttacttgttttaatacagagatatcacaatctcttgctctgcccaaacccatcccaaccccctaaaa
-41    aaaatacaattttttcctctgtttctttaatccaataaaaaCAGAGAGACCTAAGAAACGAGATCAACAAAGCCC
 35    GTCGTTTTTTTCGAGGAAAAGTGAATGACCCTTTAAGAAAATAACTCTATTGGCCGGAGAAATGGTGGAGACTCG
 110   TGGATTCTCTTAAAGTTTGTTTTTTTTTCCTCTCTTCAAAATTTTTGTTCTGTTTATACTCTGTAATGGCGTTTT
 185   AATTTGATACCTAGAAGTTAAAGTGAACAAATTTTGAGAGAAAGTCTCTTTTTTTGTTCTTCCCTGTGTGTGTG
 260   AGAGAGAGAGAGATATGGCGGTTTCAGAGCAGAGTCAAGATGTGTTTCCATGGCTTAAATCGTTACCGGTTGCTC
 335   CAGAGTTCAGACCTACTCTAGCAGAGTTTCAAGATCCGATCGCTTACATTTTGAAGATTGAAGAAGAAGCTTCTA
 410   GATATGGAATCTGTAAAATTCTGCCTCCACTGCCTCCTCCTTCCAAAAAAACCTCGATTTCTAATCTCAACCGTT
 485   CTCTGGCGGCAAGAGCGGCGGCGAGGGTTCGTGACGGCGGCTTTGGCGCGTGTGATTATGACGGTGGTCCCACAT
 560   TCGCCACGCGCCAGCAGCAGATCGGGTTTTGCCCTAGGAAACAGCGTCCAGTGCAGAGACCTGTGTGGCAGAGTG
 635   GAGAGGAGTACTCTTTTGGTGAGTTCGAGTTTAAAGCGAAGAACTTTGAGAAGAATTATCTCAAGAAATGTGGTA
 710   AAAAGAGTCAACTCTCTGCCCCTTGAAATTGAAACACTTTACTGGAGAGCCACTGTGGATAAACCCTTCTCTGTTG
 785   AGTATGCCAATGACATGCCTGGCTCGGCTTTTATCCCTCTGAGTCTGGCTGCTGCGAGGAGGAGAGAGTCTGGTG
 860   GTGAAGGAGGAACAGTTGGTGAAGACCGCTTGGAAACATGAGGGCAATGTCTAGAGCCGAAGGATCATTGCTTAAGT
 935   TCATGAAGGAAGAGATCCCTGGAGTTACATCACCAATGGTGTATGTTGCTATGATGTTTAGTTGGTTTGCTTGGC
 1010  ATGTGGAGGACCATGACCTTCATAGTCTCAATTACTTGCATATGGGTGCTGGTAAGACTTGGTACGGTGTGCCAA
 1085  AGGATGCTGCTCTGGCTTTTGAGGAGGTTGTTAGGGTTCATGGTTACGGTGAAGAGCTCAATCCTCTTGgtgagt
 1160  atgataagtgttatgtgttagtgactcatagttactcaatgtatcaattcattgttctgattgttggctttgttg
 1235  tgtctctgttcttttttgttgcttttaaatgcttttctttccctccaaaagttgtcaggggtagaagctgtatgca
 1310  agcaaactaattggttatgcctcttacattgttgtcttattagTGACATTTTCTACTCTTGGTGAGAAGACAACT
 1385  GTGATGTCTCCTGAAGTATTTGTTAAAGCCGGAATACCGTGTTGCAGgtaatggttttttatgtttgtgctctgt
 1460  ttatctcatcatcttgttgtttgcatgtctcttctttggtctcttataattggcacacttttttcttcttctggtt
 1535  tttcacgcaagtggttttttttgtatcagGTTAGTGCAAAATCCTGGAGAGTTTGTCGTCACCTTTCCGGGAGCTT
 1610  ATCATTCGGGATTTAGTCATGgtgagtaagcgacctatatttagtatcttaagtcaaccattcaaaggcctagt
 1685  atgttgaaataacctatattatccataaaaacaatcgtgggggttgtacagGATTTAATTTTTGGAGAAGCATCTA
 1760  ACATTGCCACTCCCGAATGGTTGAGAATGGCTAAAGATGCTGCTATCCGGCGAGCTGCTATAAATTACCCTCCAA
```

FIGURE 2A

```
1835  TGGTTTCTCATCTCCAGCTACTTTATGACTTTGTATTGGCTCTAGGTTCTAGgtactcttcttttctatagaca
1910  cactcaaactttttaagctgcttgaagggctcatataaggtatgtttcactcattgcagAGTGCCAACAAGCATC
1985  AATCCCAAACCACGGAGTTCTAGATTAAAAGATAAGGCAAGAAGCGAAGGAGAAAGATTGACCAAAAAGCTATTT
                                                                    •••••••
2060  GTGCAAAACATTATCCACAACAACGAATTGCTTTCTTCTCTGGGAAAAGGATCCCCAGTGGCCCTTCTCCCACAG
2135  AGTTCCTCAGATATATCAGTTTGTTCTGACCTGGGAATTGGATCCATTTGATAACCAACCAGGAGAAACCCAATC
2210  CAGTTAAAGTGTGAGGACTTAAGTTCTGATAGTGTTGTGGTTGATCTCAGTAAGGGTTTAAAGGATACAGTTTCA
2285  GTGAAAGAAAAATTTACATCTTTATGTGAAAGGAGCAGAAATCACCTAGCAAGCACGGAGAAGGACACTCAAGAA
2360  ACTCTGTCTGATGCTGAAAAGGAGGAAGAATGATGCAGCTGTTGGGCTTTGGGATCAAAGGCTTTTCTCTTGTGTT
2435  ACATGTGGAGTCTTAAGCTTTGATTGTGTAGCTATCGTTCAACCTAAAGAAGCAGCTGCTAGATATCTCATGTCT
2510  GCAGATTGTAGCTTCTTCAATGATTGGACAGCTGCTTCTGGATCTGCAAATCTTGGTCAGGCTGCAAGATCACTT
2585  CATCCTCgtaagttacaggtcgcactttcggttattggctgttatttagcatttactaacttttttttcatcatgc
2660  agAAAGCAAAGAGAAGCATGATGTAAATTACTTCTACAATGTTCCTGTTCAAACTATGGATCATTCAGTGAAGAC
2735  TGGGGATCAAAAACTTCAACAACTTCCCCGACAATAGCGCATAAAGATAATGATGTTCTTGGGATGTTAGCTTC
2810  AGCATATGGAGACTCTTCTGATTCCGAGGAAGAAGATCAAAAAGGCTTAGTTACCCCTAGTTCCAAAGGGAAAC
2885  AAAAACGTATGATCAAGAAGGTTCAGATGGCCATGAGGAGGCTAGAGATGGTAGAACTTCTGATTTTAACTGCCA
2960  GAGACTAACCAGCGAACAGAATGGGTTAAGCAAAGGCGGAAAAATCATCACTTCTGGAAATAGCTTTACCATTTAT
3035  TCCAAGATCTGATGACGATTCATGTCGGTTGCACGTGTTTTGTCTTGAGCATGCTGCGGAAGTGGAACAGCAACT
3110  TGGTCCTTTTGGGGGGATTAACTTAATGTTACTGTGCCATCCAGgtaacatcaaaactacaagattcattttatt
3185  agtatttctgtatcagttatgcaattctttagtctttttcatcatttttgacgcacaacatttgcagAGTACCCCA
3260  GGATAGAGGCTGAAGCAAAGATAGTTGCCGAAGAGCTGGTCATCAATCACGAATGGAATGATACTGAATTCAGGA
3335  ATGTGACCCGAGAGGATGAGGAAAACGATTCAGGCAGGGTTGGATAATGTTGAAGCTAAGGGTGGGAACAGTGATT
3410  GGACCGTAAAATTGGGTGTTAACCTTTTCTTACAGGGCTATTCTCAGTGCGCTCTCGTCTGTACAGTAAGCAGATGC
3485  CGTATAACTCCATCATATACAAGGCGTTCGGTCGCAGCTCTCCAGTAGCGAGCTCACCCTGGAAACCAAAGTCT
3560  CTGGTAAAAGATCGTCCAGACAGGAGGAAATATGTTGTTGGAAAATGGTGTGGTAAGGTTTGGATGTCACATCAGg
3635  tactattgtctaacctgaatccatactaattcagacattagtacacttctgtttggttcaatttgcttttctttc
3710  ttcagGTGCATCCCTTTTTGCTGGAGCAGGACTTAGAGGGGGAAGAATCTGAAAGAAGTTGTCATCTTCGAGTTG
3785  CTATGGATGAGGATGCCACTGGAAAGAGATCGTTTCCTAATAATGTTTCCAGGGATTGGACAACAATGTTTGGAA
3860  GAAAGTATTGTAGGAAAGAGAAAGATAAGAGCAAAGGCGGTGCCACGCAAGAAGCTTACTTCTTTTAAGAGGGAAG
3935  ATGGAGTTTCTGATGACACATCAGAAGATCATTCTTATAAGCAGCAATGGAGGGCTTCCGGGAATGAGGAAGAGT
4010  CTTATTTTGAGACAGGGAAACACAGCTTCTGGTGATTCATCAAATCAAATGTCTGATCCGCACAAGGGAATTATCA
4085  GACATAAAGGTTATAAAGAATTTGAGTCAGATGATGAGGTTTCAGACCGGTCACTTGGGGAAGAGTATACTGTAC
4160  GGGCATGTGCAGCTTCAGAGAGCTCAATGAGAATGGCTCTCAGCATTCAATGTATGACCATGATGATGATGATG
4235  ATGATATCGACAGGCAGCCTAGGGGGATTCCAAAGGAGCCAACAGACAAGAGTTTTTAGGAAATCCAGTTTCATATG
4310  AGTCAGAAGATAATGGCGTTTATCAGCAAAGGCGGAAGAATATCCATAAGTAATAGGCAAGCTAATCGAATGGTTG
```

FIGURE 2B

```
4385   GTGAATATGATTCAGCAGAGAATTCTTTGGAGGAACGAGGCTTTTGCAGTACAGGGAAAAGGCAAACCAGGTCAA
4460   CAGCCAAAGGAATAGCAAAAACCAAGACAGTTCAGAGTTGGAGAGACACAAAAGGTCGCTTTTTTGCAAGAATTTG
4535   CATCTGGAAAGAAGAATGAAGAATTGGATTCATACATGGAGGGACCTAGCACACGGCTTAGGGTGAGACATCAGA
4610   AGCGGTGGAGGAGGGGTCTTTAGAAAACAAAACCAAAGAAGATTGGTAAGAAGAGAAGTGGTAATGCTTCCTTCTCCA
4685   GAGTTGCAACTGAAAAAGATGTGGAGGAAAAAGAAGAAGAAGAAGAAGAAGAATGAGGAAGAGGAATGTGCAG
4760   CATAGCAATGTAACATGGAGGGTTGCAGGATGAGTTTCAGTTGGGAAAAACAGTTGATGTTACACAAAAGAAACA
4835   TATGCCCAATTAAAGGCTGTGGTAAAAACTTCTTCTCACACAAGTATTTGGTTCAACACCAGCGTGTTCACTCAG
4910   AGGACGGTCCTCTGAAATGTCCATGGAAGGGATGTAAGATGACGTTCAAGTGGGCTTGGTCTAGAACCGAGCACA
4985   TAAGGGTTCACACAGGCGCTAGGCCTTATGTTTGGCTGAACCGGATTGTGGTCAAACATTCAGGTTTGTCTCTG
5060   ACTTCAGCCGGCATAAAAGGAAGACCGGTCATTGGGTTAAGAAGACCAACAAAAGGTGATTTAGGCTCTAACATG
5135   GAATCTATCATGAAGAAGATTACTCCATTGATCTATTAGAAGAAAATTGGATTGTAGGAATATTAGGGGTTTTCT
5210   AAGTGTGTATGTCTCTCTGGTCCTCTGTCAATTCGGGATTATAAAGTCAAAGTCTTAACATTTGGAATAGCCATT
5285   GTTTGTTGCAGAGGTTTTCACTTTCAGACAGATTCTCTCTTTGTTGTATTCTCTATttttgcagttgaatgaatc
5360   tgtaacaacaacaaatcctggtgtaggaaaagcattgtgttactcaagtatttgacatatatggttgtatacgtg
5435   gcttatcctggttggttgacagtcagagttcatcgccgtggacttcatttgactttgataaagactcaaacctac
5510   caaattgctaatgaatgacattacctgtgtcaactaggatgtaaaactctctgacttcagcacacggcacaaacg
5585   aaag
```

A.

```
1     MAVSEQSQDV  PPWLKSLPVA  PEFRPTLAEF  QDPIAYILKI  EEEASRYGIC  KILPPLPPPS
61    KKTSISNLNR  SLAARAAARV  RDGGPGACDY  DGGPTPATRQ  QQIGPCPRKQ  RPVQRPVWQS
121   GEEYSFGEFE  PKARNFEKNY  LKKCGKKSQL  SALEIETLYW  RATVDKPFSV  EYANDMPGSA
181   FIPLSLAAAR  RRESGGEGGT  VGETAWNMRA  MSRAEGSLLK  FMKEEIPGVT  SPMVYVAMMF
241   SWFAWHVEDH  DLHSLNYLHM  GAGKTWYGVP  KDAALAFEEV  VRVHGYGEEL  NPLVTFSTLG
301   EKTTVMSPEV  FVKAGIPCCR  LVQNPGEFVV  TPPGAYHSGF  SHGFNFGEAS  NIATPEWLRM
361   AKDAAIRRAA  INYPPHVSHL  QLLYDFVLAL  GSRVPTSINP  KPRSSRLKDK  ARSEGERLTK
421   KLFVQNIIHN  NELLSSLGKG  SPVALLPQSS  SDISVCSDLR  IGSHLITNQE  NPIQLKCEDL
481   SSDSVVVDLS  NGLKDTVSVK  EKFTSLCERS  RNHLASTEKD  TQETLSDAER  RKNDAAVALS
541   DQRLPSCVTC  GVLSFDCVAI  VQPKEAAARY  LMSADCSFFN  DWTAASGSAN  LGQAARSLHP
601   QSKEKHDVNY  FYNVPVQTMD  HSVKTGDQKT  STTSPTIAHK  DNDVLGMLAS  AYGDSSDSEE
661   EDQKGLVTPS  SKGETKTYDQ  EGSDGHEEAR  DGRTSDFNCQ  RLTSEQNGLS  KGGKSSLLEI
721   ALPFIPRSDD  DSCRLHVFCL  EHAAEVEQQL  RPFGGINLHL  LCHPEYPRIE  AEAKIVAEEL
781   VINHEWNDTE  FRNVTREDEE  TIQAALDNVE  AKGGNSDWTV  KLGVNLSYSA  ILSRSPLYSK
841   QMPYNSIIYK  AFGRSSPVAS  SPSKPKVSGK  RSSRQRKYVV  GKWCGKVWMS  HQVHPFLLEQ
901   DLEGEESERS  CHLRVAMDED  ATGKRSFPNN  VSRDSTTMFG  RKYCRKRKIR  AKAVPRKKLT
961   SPKREDGVSD  DTSEDHSYKQ  QWRASGNEEE  SYFETGNTAS  GDSSNQMSDP  HKGIIRHKGY
1021  KEFESDDEVS  DRSLGEEYTV  RACAASESSM  ENGSQHSMYD  HDDDDDDIDR  QPRGIPRSQQ
1081  TRVFRNPVSY  ESEDNGVYQQ  SGRISISNRQ  ANRMVGEYDS  AENSLEERGF  CSTGKRQTRS
1141  TAKRIAKTKT  VQSSRDTKGR  FLQEFASGKK  NEELDSYMEG  PSTRLRVRHQ  KPSRGSLETK
1201  PKKIGKKRSG  NASPSRVATE  KDVEEKEEEE  EEENEEEECA  AYQCNMEGCT  MSFSSEKQLM
1261  LHKRNICPIK  GCGKNFFSHK  YLVQHQRVHS  DDRPLKCPWK  GCKMTFKWAW  SRTEHIRVHT
1321  GARPYVCAEP  DCGQTFRFVS  DFSRHKRKTG  HSVKKTNER*
```

```
1    HAVSEQSQDV FPWLKSLPVA PEFRPTLAEP QDPIAYILKI EEEASRYGIC KILPPLPPPS
61   KKTSISHLHR SLAARAAARV RDGGFGACDY DGGPTFATRQ QQIGPCPRKQ RPVQRPVHQS
121  GEEYSPGEFE PKAKNPEKNY LKKCGKKSQL SALEIETLYH RATVDKPFSV EYANDHPGSA
181  PIPLSLAAAR RRESGGEGGT VGETAHHHRA HSRAEGSLLK FHKEEIPGVT SPHVYVAHHP
241  SWPAHHVEDH DLHSLHYLHH GAGKTHYGVP KDAALAPEEV VRVHGYGEEL NPLVTFSTLG
301  EKTTVHSPEV FVKAGIPCCR LVQNPGEFVV TFPGAYHSGP SHGFNPGEAS NIATPEWLRH
361  AKDAAIRRAA INYPPHVSHL QLLYDFVLAL GSRVPTSINP KPRSSRLKDK ARSEGERLTK
421  KLFVQNIIHN NELLSSLGKG SPVALLPQSS SDISVCSDLR IGSHLITHQE NPIQLK*
```

FIGURE 4

```
EIN6      1264 .KRNECPIKGCGKN...FFSHKYLVQHQRVHSDDRPLKCPWKGCKMTRKWAWSRTEHIR.
GLI1       269 .KEFYCHWGGCSRELRPFKAQYMLVVHMRRHTGEKPHKCTFEGCRKSYSRLENLKTHLR.
X84986     353 .RPFKCPFEGCGRS...FTMSNLRKVHIRTHTGEKPYYCSEPGCGRAFASATNYKNHVR.
GLI3       510 KKEFYCRFLDCSREQKPFKAQYMLVVHMRRHTGEKPHKCTFEGCTKAYSRLENLKTHLR.
SPH1-BF    237 ERPFKCPFEGCGRS...FTMSNLRKVHMRTHTGEKPYYCTEPGCGRAFASATNYKNEVR.
RPH1p      704 ........................GKNKIYIC..KECQRKFSSCHHLTRHKES

EIN6      1319 VHTGARPYVCAEEDCGQTFRFVSDFSRHKRKTG.HSVKK
GLI1       327 SHTGEKPYMCEQEGCSKAFSNASDRAKHQN.RT.HSNEK
X84986     408 IHTGEKPYVCTVPGCDKRFTEYSSLYKHH..VV.HIHS.
GLI3       569 SHTGEKPYVCEHEGCNKAFSNASDRAKHQN.RT.HSNEK
SPH1-BF    293 IHTGEKPYVCTVPGCDKRFTEYSSLYKHH..VV.PIHS.
RPH1p      731 VHSCEKPHSC..EKCGKRFKRRD....H...VLQH....
```

FIGURE 5

```
EIN6        1 MAVSEQSQDVFPWLKSEPVAPEFRPTLAEFQDPLAYILKIEEEASEYGICKILPPLPPPS
RBP2       17 ...............PECPVFEPSWEEFTDPLSEIGEIRPEAEKTGICKIRPP.....
Smcx       12 ...............PECPVFEPSWAEFRDPLEYIAKIRPIAEKSGICKIRPP.....
CG9088    159 ...............PECPVFRPTTEEFKNPLAYISKIRSIAEKCGIAKIEPP.....
AL136078   54 ........IHGEFVAPVFYPDKEEFQDSRGYINKIAPIGEKYGIIKIVPP.....
F2K11.14   27 ...............NLELGPVLYPTEEEFKDPLEYIHKIKEEAEVYGICKIVPP.....

EIN6       61 KKTSISNLNRSLAARAAARVRDGGFGACDYDGGPTFATRQQQIGFCPRKQRPVQRPV...
RBP2          ............................................................
Smcx          ............................................................
CG9088        ............................................................
AL136078      ............................................................
F2K11.14      ............................................................

EIN6      118 WQSGEEYSFGEFEFKAKNFEKNYLKKCGKKSQESALEEETLEWRAT..NEKPFSVEYAND
RBP2      356 .QAVREYTLQSFGEMADNFKSEYFNMP...VHMVPTEEVEKEFWRLVSSIEEDVIVEYGAD
Smcx      387 .QATREYTLQSFGEMADSFKAEYFNMP...VHEVPTEEVEKEFWRLVNSIEEDVIVEYGAD
CG9088    511 .QAEREYTLCQFGCMADCFKQEYFRKP...VHEVPTEEVEREFWRKVSSIEEDVEVEYGAD
AL136078  344 FETGNYYTLSNEEKYCDNFKKNYESKFK.DSEETEEEVEKEEWRLVKDNNTSEEVEYGAD
F2K11.14  324 ..........................VSRTQEEKKFWEEIVEGSGGEVEVMYGND EIN6      176 MP....GSAFIPESLAAARRRESEGEGGTVEEEEWNMRAMSRAEGSELKFMKEEIPGVIS
RBP2      413 ESEKDEGSGFFVKDGR...RKELEEEE.EYALSGWNLNNMPVLEQSYLAHINVDISGMKV
Smcx      444 IHEKEEGSGFPVSDSK...RHETPEEE.EYATSGWNLNVMPVLEQSYLCHINADISGMKV
CG9088    568 LHTMDHGSGFPTKSS....LYELPGEQ.EYAESSWNLNNEPLLEDSEEGHINADISGMNA
AL136078  403 LSTLDQGSAEESEAKN...PVNP......YSKDTWNLNVHASTNGSELSYLENPESGEIC
F2K11.14  352 LDTSVEGSGFPREGDQRPESVEADIWE.EYCGSPWNLNNMEKLKGSMLQAIRHNINGYTV EIN6      232 PMLYVAMMFSWFAWHIEDHDLHSENYLHMGAEKTWYGVPKDAALAFEEVIPRVHEYGEELN
RBP2      469 PWLYVGMCFSSFCWHIEDHWSYSINYLHWGEPKTWYGVPSHAAEQLEEVMREEAP.ELFE
Smcx      500 PWLYVGMCVFSAFCWHIEDHWSYSINYLHWGEPKTWYGVPSLAAEHLEEVMEKETP.ELFE
CG9088    623 PWEYVGMCFEAFCWHNEDHWSYSINYLHWGEPKTWYGVPGSCAEEFEETMRQAAP.ELFS
AL136078  454 PWLYVGMCFSTFCWHVEDNYTYSMNYQEEGETKLWYGEPGDQAERFERAALDMAP.ELVK
F2K11.14  411 PWLYEGMLFSSFCWHFEDHCFYSMNYLHWGEAKCWYGEPGSAASAFEKVMRKTLP.ELFE EIN6      292 PLVTFSTLGEKTTYMSPEVFMKAGEPCCRLVQNPGEFVVTFPGAYHSGFSHGENFGEASN
RBP2      527 ..SQPDLLHQLVTEMNPNVLMEHGVPVYRTNQCAGEFVVTFPRAYHSGFNQGYNFAEAVN
Smcx      558 ..SQPDLLHQLVTEMNPNTLMSHGVPVYRTNQCAGEFVITFPRAYHSGFNQGYNFAEAVN
CG9088    681 ..SQPDLLHQLVTEMNPNELMNNRVPVERTDQHAGEFVITFPRAYHAGFNQGYNFAEAVN
AL136078  512 ..KQKDLLYQLATMENPEELQKRGVDVYFIDQGPNEFVITFPKSEHACINHGENINEAVN
F2K11.14  469 ..AQPDLLFQLVTMISETVLQENKVPVYTVLQEPGNFVITFPKSEHAGFNFGLNCAEAVN EIN6      352 IATPEWLRMAK..DAAIERAAENYEPNVSHLEILYDFVLALGSRVPTS...........
RBP2      586 FCTADWLPEGR..SCVNHYRRLRRHCVFSHEELEF...........
Smcx      617 FCTADWLPAGR..SCIEHYRRLRRYCVFSHEELIC...........
CG9088    740 FAPADWIKKGR..ECVNHYSMLRRFCVFSHEELVCKEAL...........
AL136078  571 FAPKDWLLNCFSLNGVLKYQSLLKPPVLSHEMLVYNEATNPASEISVS...........
F2K11.14  528 FATADWLPYGG..SGAELYRLYRKPSVISHEELECVVAKGNCCNNEGSIHLKKELLRIYS EIN6          ............
RBP2          ............
Smcx          ............
CG9088        ............
AL136078      ............
F2K11.14  586 KEKTWREQLWK
```

FIGURE 6

```
EIN6        1   MAVSEQSQEVFPWLKSLPVAPEFRPTLAEFQDPIAYILKIEEEA..SRYGICKDCPP...
RPH1p      15   ..................PVFKPTYEGFEDFYAYCKAINKYG..MKSGVVKVIPPKEW
F19I3.11   61   ..................APVFHPTSEEFEDTLAYIEKIRPLA..ESFGICRIVPPSIW
CG4037      3   ....KMS.EVP.......RIKVFRPTWEEFIDFPKYVAYMESQG.AHKAGLAKVVPPPEW
Y48B6A.11  90   ..................FYPTIREFKIESQVIKKIEQNGGHLKAGIAKIVAPECW
KIAA0780   54   MEV....EVESPLNPSCKIMTFRPSMEEFREFNKYIAYMESKG.AHRAGLAKVIPPKEW

EIN6       56   LPPPE..KKISESNLNREIAARAAARVRDGGFGACDYDGGPTFATRQQ.QIGFCPEKQEP
RPH1p      53   KDKLD.LPYSAETLQKIKIKSPIQOHISG.......NKGLEMVQNVEKNKTYNIIQWKD
F19I3.11  100   SPPCR..LKGDSIWKNKNFPTRIQFVDLLQ.......NRGPVKKKTPKGRKRKRGKYSRT
CG4037     50   VPRRE..GMADEDALNVIIPAPICQWVTG.......KQGYFQQINIQ.KKPITVKQFSE
Y48B6A.11 128   TPRPIRKDESDVDDYEIIQPARETIEATE.......KPGAMFKRNVTCRRKIPVRBFRT
KIAA0780  109   KPRQ...CYDDID..NILIPAPIQQMVTG.......ISGLITQYNIQ.KKAMTVKEFRQ

EIN6      113   VQRPVWQ.............................SGEEYSFGEFEFKAKNFEKNYLKK
RPH1p     104   LSKDYVPPEDPKARRNSRKGSVSKSTKLKLKNFESSFNIEDFEQFRTEYTIDLSD..FQN
F19I3.11  151   VAPKK........RNGSVSKSVSTPKATEEENFGFESGPEFTLEKFEKYAQDFKDSYFER
CG4037     99   LASI........................................ERYATEK.H..FDF
Y48B6A.11 180   LANS........................................AQVRNERPD..LKG
KIAA0780  155   LANS........................................GKYCTER.Y..LEY

EIN6      144   CGKKSQLSALEIETLYWRATVDK..PFSVEYANDVPGSAIIPLSLAAARRRESGGEGGTV
RPH1p     162   TERL......KFEEEYYWKTIN....ETTPMYGADTPGSIEPEGINV............
F19I3.11  203   KDNVGDPSVEEIEGEYWRIIEKETNEVKVIYGTDIENPILGSGFSKGVKIPTRRNDMDKY
CG4037    114   ED........EERKYWKNIT....EVAPIYGADYSGSITDTDQES.............
Y48B6A.11 196   SE........EEKHYEDNIL....HGEPIYGADTEGSFYDAQVEE.............
KIAA0780  170   ED........EERKYWKNIT....EVAPIYGADINGSIYDEGVIE.............

EIN6      202   GETAWNMRAMSRAEGSILKFMKEEIPGVTSEMYYVAMMFSWFAWHYEDHDLHSENYLHMG
RPH1p     198   ....WNYAKLPNILD....HMETKYPGVNDSYLYAGEWKASFSWHEEDQDLYSINYIHFG
F19I3.11  263   ISSGWNINNLARBQGSILSFEDCEISGVGVPWLYVGMCFSTFCWHVEDNHLYSENYHHFG
CG4037    146   ....WNINRLGTILDYVNKIYNIEIDGVNTAYLYFGMWKTTFAWHTEDMDLYSINYLHFG
Y48B6A.11 228   ....WNYNRLGTIL....EETNYEIKGVNTVYLYFGMYKTTFPWHAEDMDLS.INELHFG
KIAA0780  202   ....WNINARLNTYLDVVEEECGISIEDGVNTPYLYFGMWKTTFAWHTEDMDLYSINYLHFG

EIN6      262   AGKIWYGVPKEAALAFEEVRVHGYGEELNPLVTFSTLGEKTTVMSPEYFVKAGIPCCRI
RPH1p     251   APKQWYSIPQEDRFEFYKFMGEQFEEE...AKNGPEFLRHKMFLASPKDLQENGIRCNEI
F19I3.11  323   EPKVWYGVPGSHATGLEKAMRKHLPDL...FDEQPDLIHELVIQFSPTILKNEGYPVYRA
CG4037    203   APKIWVIPPECSRKLEKVANQYFPAS...YKNCNAYLRHKMTLISPQILKQHDVPVSKI
Y48B6A.11 280   APKYWEAISSEHADRFERFMSQQFSYQNEYAPECKAFLRHKTYLVIPELLRQAGIPYATM
KIAA0780  259   EPKSWYAIPPEHGKRLERLAGGFFSS...SQGCDAFLRHKMTLISPSVLKKYGIPFDKI

EIN6      322   VQNPGEFVVTFPGAYHSGFSHGFNFSEASNIATPEWERMAKDAAI
RPH1p     308   VHHEGEFMITYPYGYHAGFNYGYNLAESVNFALEEWLPIGKKA..
F19I3.11  380   VQNAGEYVVTFPRAYHSGFNGGFNCAEEVNVAPVDWLAHGQNA..
CG4037    260   TQEAGEIMITFPEGYHAGFNHGFNCAESTNFAMERWIEYGKRA..
Y48B6A.11 340   VQRPNEFIITFPRGYHMGFNLGYNLAESTNFASQRWIEYGKDAVI
KIAA0780  316   TQEAGEFMITFPYGYHAGFNHGFNCAESTNFAIVRWIEYGKVAKI
```

FIGURE 7

SEQUENCE LISTING

<160> NUMBER OF SEQ ID NOS: 23

<210> SEQ ID NO 1
<211> LENGTH: 6829
<212> TYPE: DNA
<213> ORGANISM: Arabidopsis thaliana

<400> SEQUENCE: 1

```
atggtcgggg aatcccattg gaaagtgagt ggatactaca cattttagtt ttatggcttg      60
gagtccagaa cctccgcatg tttctaaagc tatatattga ttttttgttt tggttgccat     120
aggtaccggg gaaagaggat gaggatcgac tattttctgg tctctgaaca actcaaagac     180
cgtatagttt cttgtaagat gcacggtcgt gggatagaac ttgaaggtgc catagataaa     240
cctgttcatc acacagattc atagaagatt attattagct cttttgcaa caatttggtt      300 cttgatttgt ttcaggtttc catgggagtg atcattgtcc ggttacactc gagctttcga     360
agccatcttc agaaatggaa cagaaccagg tgtcaaacta aaatcatctt cttctgtatt     420
agaacataag gccttcttag gaacaagcca aagcttattt tatcagagaa tttaattttt     480
actttgccga gagatgcatt gaagatttga ttgaggttat tgagacactt atttagcctt     540
gttactctga tgaactctca aatgtactta taattattgt tgtgcttatc ttaatatgtt     600
ttattttcct aagaaatgtt gatattttta attgtgaatc ttcttcattt aattattttt     660
```

-continued

```
atttattaac ttttgagtca tttctaaaga tttagagctt ttgttggtgt attttaagca        720
tattataccc tttgctttat tgtcttagtc agtaggtaga ggcaacattc gttaaaccaa        780
tggctcattc aaattctttt ttttgggctc attcatattc ataaaaatca aatttggatt        840
cagcataaca aacacaataa taaatgtaga catttatatc atacattaat ttctactaat        900
ttcatgaact accaaagact aaaaatgttt aatgagaaat atcttttta aaaccatcaa         960 aaattttact cttaaaattg ggatttatgt ttggttttaa aaaggagttt ttgaatgtgc       1020
aaacggattt acagagagga caacaacaaa tgtgtgttag aaatggcaga atcgtaaata       1080
ataagaaaat cataccctt taaaaaccat ttctctctct aactaagtgt tctttacttg        1140
ttttaataca gagatatcac aatctcttgc tctgcccaaa cccatcccaa cccccctaaaa      1200 aaaatacaat tttttcctct gtttctttaa tccaataaaa acagagagac ctaagaaacg       1260
agatcaacaa agcccgtcgt ttttttcgag gaaagtgaa tgacccttta agaaaataac        1320
tctattggcc ggagaaatgg tggagactcg tcgattctct taaagtttgt ttttttttcc       1380
tctcttcaaa attttgttc tgtttatact ctgtaatggc gttttaattt gatacctaga        1440
agttaaagtg aacaaatttt gagagaaagt ctcttttttt tgttcttccc tgtgtgtgtg       1500
agagagagag agatatggcg gtttcagagc agagtcaaga tgtgtttcca tggcttaaat       1560
cgttaccggt tgctccagag ttcagaccta ctctagcaga gtttcaagat ccgatcgctt       1620
acattttgaa gattgaagaa gaagcttcta gatatggaat ctgtaaaatt ctgcctccac       1680
tgcctcctcc ttccaaaaaa acctcgattt ctaatctcaa ccgttctctg gcggcaagag       1740
cggcggcgag ggttcgtgac ggcggctttg gcgcgtgtga ttatgacggt ggtcccacat       1800
tcgccacgcg ccagcagcag atcgggtttt gccctaggaa acagcgtcca gtgcagagac       1860
ctgtgtggca gagtggagag gagtactctt ttggtgagtt cgagtttaaa gcgaagaact       1920
ttgagaagaa ttatctcaag aaatgtggta aaaagagtca actctctgcc cttgaaattg       1980
aaacacttta ctggagagcc actgtggata aacccttctc tgttgagtat gccaatgaca       2040
tgcctggctc ggcttttatc cctctgagtc tggctgctgc gaggaggaga gagtctggtg       2100
gtgaaggagg aacagttggt gagaccgctt ggaacatgag ggcaatgtct agagccgaag       2160
gatcattgct taagttcatg aaggaagaga tccctggagt tacatcacca atggtgtatg       2220
ttgctatgat gtttagttgg tttgcttggc atgtggagga ccatgacctt catagtctca       2280
attacttgca tatgggtgct ggtaagactt ggtacggtgt gccaaaggat gctgctctgg       2340
cttttgagga ggttgttagg gttcatggtt acggtgaaga gctcaatcct cttggtgagt       2400
atgataagtg ttatgtgtta gtgactcata gttactcaat gtatcaattc attgttctga       2460
ttgttggctt tgttgtgtct ctgttctttt tgttgctttt aaatgctttt ctttccctcc       2520
aaaagttgtc agggtagaa gctgtatgca agcaaactaa ttggttatgc ctcttacatt        2580
gttgtcttat tagtgacatt ttctactctt ggtgagaaga caactgtgat gtctcctgaa       2640
gtatttgtta aagccggaat accgtgttgc aggtaatggt tttttatgtt tgtgctctgt       2700
ttatctcatc atcttgttgt ttgcatgtct cttctttggt ctcttataat tggcacactt       2760
tttcttcttc tggttttca cgcaagtggt tttttgtat caggttagtg caaaatcctg         2820
gagagtttgt cgtcaccttt ccgggagctt atcattcggg atttagtcat ggtgagtaag       2880
cgacctatat ttagtatctt taagtcaacc attcaaaggc ctagtatgtt gaaataactt       2940
atattatcca taaaaacaat cgtgggggtt gtacaggatt taattttgga gaagcatcta      3000
acattgccac tcccgaatgg ttgagaatgg ctaaagatgc tgctatccgg cgagctgcta      3060
```

```
taaattaccc tccaatggtt tctcatctcc agctacttta tgactttgta ttggctctag    3120
gttctaggta ctctttcttt tctatagaca cactcaaact ttttaagctg cttgaagggc    3180
tcatataagg tatgtttcac tcattgcaga gtgccaacaa gcatcaatcc caaaccacgg    3240
agttctagat taaaagataa ggcaagaagc gaaggagaaa gattgaccaa aaagctattt    3300
gtgcaaaaca ttatccacaa caacgaattg ctttcttctc tcggaaaagg atccccagtg    3360
gcccttctcc cacagagttc ctcagatata tcagtttgtt ctgacctgcg aattggatcc    3420
catttgataa ccaaccagga aaacccaatc cagttaaagt gtgaggactt aagttctgat    3480
agtgttgtgg ttgatctcag taacggttta aaggatacag tttcagtgaa agaaaaattt    3540
acatctttat gtgaaaggag cagaaatcac ctagcaagca cggagaagga cactcaagaa    3600
actctgtctg atgctgaaag gaggaagaat gatgcagctg ttgcgctttc ggatcaaagg    3660
cttttctctt gtgttacatg tggagtctta agctttgatt gtgtagctat cgttcaacct    3720
aaagaagcag ctgctagata tctcatgtct gcagattgta gcttcttcaa tgattggaca    3780
gctgcttctg gatctgcaaa tcttggtcag gctgcaagat cacttcatcc tcgtaagtta    3840
caggtcgcac tttcggttat tggctgttat ttagcattta ctaactttt ttcatcatgc    3900 agaaagcaaa gagaagcatg atgtaaatta cttctacaat gttcctgttc aaactatgga    3960
tcattcagtg aagactggcg atcaaaaaac ttcaacaact tccccgacaa tagcgcataa    4020
agataatgat gttcttggga tgttagcttc agcatatgga gactcttctg attccgagga    4080
agaagatcaa aaaggcttag ttaccccctag ttccaaaggg gaaacaaaaa cgtatgatca    4140
agaaggttca gatggccatg aggaggctag agatggtaga acttctgatt ttaactgcca    4200
gagactaacc agcgaacaga atgggttaag caaaggcgga aaatcatcac ttctggaaat    4260
agctttacca tttattccaa gatctgatga cgattcatgt cggttgcacg tgttttgtct    4320
tgagcatgct gcggaagtgg aacagcaact tcgtcccttt gggggattaa acttaatgtt    4380
actgtgccat ccaggtaaca tcaaaactac aagattcatt ttattagtat tctgtatca    4440 gttatgcaat tctttagtct ttttcatcat tttgacgcac aacatttgca gagtaccca    4500 ggatagaggc tgaagcaaag atagttgccg aagagctcgt catcaatcac gaatggaatg    4560
atactgaatt caggaatgtg acccgagagg atgaggaaac gattcaggca gcgttggata    4620
atgttgaagc taagggtggg aacagtgatt ggaccgtaaa attgggtgtt aacctttctt    4680
acagcgctat tctcagtcgc tctcctctgt acagtaagca gatgccgtat aactccatca    4740
tatacaaggc gttcggtcgc agctctccag tagcgagctc accctcgaaa cccaaagtct    4800
ctggtaaaag atcgtccaga cagaggaaat atgttgttgg aaaatggtgt ggtaaggttt    4860
ggatgtcaca tcaggtacta ttgtctaacc tgaatccata ctaattcaga cattagtaca    4920
cttctgtttg gttcaatttg ctttttctttc ttcaggtgca tccctttttg ctggagcagg    4980
acttagaggg ggaagaatct gaaagaagtt gtcatcttcg agttgctatg gatgaggatg    5040
ccactggaaa gagatcgttt cctaataatg tttccaggga ttcgacaaca atgtttggaa    5100
gaaagtattg taggaagaga aagataagag caaaggcggt gccacgcaag aagcttactt    5160
cttttaagag ggaagatgga gtttctgatg acacatcaga agatcattct tataagcagc    5220
aatggagggc ttccgggaat gaggaagagt cttatttga gacagggaac acagcttctg    5280
gtgattcatc aaatcaaatg tctgatccgc acaagggaat tatcagacat aaaggttata    5340
aagaatttga gtcagatgat gaggtttcag accgttcact tggggaagag tatactgtac    5400
```

-continued

```
gggcatgtgc agcttcagag agctcaatgg agaatggctc tcagcattca atgtatgacc    5460
atgatgatga tgatgatgat atcgacaggc agcctagggg gattccaagg agccaacaga    5520
caagagtttt taggaatcca gtttcatatg agtcagaaga taatggcgtt tatcagcaaa    5580
gcggaagaat atccataagt aataggcaag ctaatcgaat ggttggtgaa tatgattcag    5640
cagagaattc tttggaggaa cgaggctttt gcagtacagg gaaaaggcaa accaggtcaa    5700
cagccaaacg aatagcaaaa accaagacag ttcagagttc gagagacaca aaaggtcgct    5760
ttttgcaaga atttgcatct ggaaagaaga atgaagaatt ggattcatac atggagggac    5820
ctagcacacg gcttagggtg agacatcaga agccgtcgag agggtcttta gaaacaaaac    5880
caaagaagat tggtaagaag agaagtggta atgcttcctt ctccagagtt gcaactgaaa    5940
aagatgtgga ggaaaagaa gaagaagaag aagaagagaa tgaggaagag gaatgtgcag    6000
cataccaatg taacatggag ggttgcacga tgagtttcag ttcggaaaaa cagttgatgt    6060
tacacaaaag aaacatatgc ccaattaaag gctgtggtaa aaacttcttc tcacacaagt    6120
atttggttca acaccagcgt gttcactcag acgaccgtcc tctgaaatgt ccatggaagg    6180
gatgtaagat gacgttcaag tgggcttggt ctagaaccga gcacataagg gttcacacag    6240
gcgctaggcc ttatgtttgc gctgaaccgg attgtggtca acattcagg tttgtctctg     6300
acttcagccg gcataaaagg aagaccggtc attcggttaa gaagaccaac aaaaggtgat    6360
ttaggctcta acatggaatc tatcatgaag aagattactc cattgatcta ttagaagaaa    6420
attggattgt acgaatatta ggggtttct aagtgtgtat gtctctctgg tcctctgtca     6480
attcgggatt ataaagtcaa agtcttaaca tttggaatag ccattgtttg ttgcagacgt    6540
tttcactttc agacagattc tctctttgtt gtattctcta ttttttgcagt tgaatgaatc    6600
tgtaacaaca acaaatcctg gtgtaggaaa agcattgtgt tactcaagta tttgacatat    6660
atggttgtat acgtggctta tcctggttgg ttgacagtca gagttcatcg ccgtggactt    6720
catttgactt tgataaagac tcaaacctac caaattgcta atgaatgaca ttacctgtgt    6780
caactaggat gtaaaactct ctgacttcag cacacggcac aaacgaaag                6829
```

<210> SEQ ID NO 2
<211> LENGTH: 93
<212> TYPE: PRT
<213> ORGANISM: Arabidopsis thaliana
<220> FEATURE:
<221> NAME/KEY: ZN_FING
<222> LOCATION: (1)...(93)

<400> SEQUENCE: 2

```
Lys Arg Asn Ile Cys Pro Ile Lys Gly Cys Gly Lys Asn Phe Phe Ser
 1               5                  10                  15

His Lys Tyr Leu Val Gln His Gln Arg Val His Ser Asp Asp Arg Pro
            20                  25                  30

Leu Lys Cys Pro Trp Lys Gly Cys Lys Met Thr Phe Lys Trp Ala Trp
        35                  40                  45

Ser Arg Thr Glu His Ile Arg Val His Thr Gly Ala Arg Pro Tyr Val
    50                  55                  60

Cys Ala Glu Pro Asp Cys Gly Gln Thr Phe Arg Phe Val Ser Asp Phe
65                  70                  75                  80

Ser Arg His Lys Arg Lys Thr Gly His Ser Val Lys Lys
                85                  90
```

<210> SEQ ID NO 3

```
<211> LENGTH: 95
<212> TYPE: PRT
<213> ORGANISM: Mus musculus
<220> FEATURE:
<221> NAME/KEY: ZN_FING
<222> LOCATION: (1)...(95)

<400> SEQUENCE: 3
```

Lys Glu Phe Val Cys His Trp Gly Gly Cys Ser Arg Glu Leu Arg Pro
1               5                   10                  15

Phe Lys Ala Gln Tyr Met Leu Val Val His Met Arg Arg His Thr Gly
            20                  25                  30

Glu Lys Pro His Lys Cys Thr Phe Glu Gly Cys Arg Lys Ser Tyr Ser
        35                  40                  45

Arg Leu Glu Asn Leu Lys Thr His Leu Arg Ser His Thr Gly Glu Lys
    50                  55                  60

Pro Tyr Met Cys Glu Gln Glu Gly Cys Ser Lys Ala Phe Ser Asn Ala
65              70                  75                  80

Ser Asp Arg Ala Lys His Gln Asn Arg Thr His Ser Asn Glu Lys
                85                  90                  95

```
<210> SEQ ID NO 4
<211> LENGTH: 90
<212> TYPE: PRT
<213> ORGANISM: Drosophila melanogaster
<220> FEATURE:
<221> NAME/KEY: ZN_FING
<222> LOCATION: (1)...(90)

<400> SEQUENCE: 4
```

Arg Pro Phe Lys Cys Pro Phe Glu Gly Cys Gly Arg Ser Phe Thr Thr
1               5                   10                  15

Ser Asn Ile Arg Lys Val His Ile Arg Thr His Thr Gly Glu Arg Pro
            20                  25                  30

Tyr Tyr Cys Ser Glu Pro Gly Cys Gly Arg Ala Phe Ala Ser Ala Thr
        35                  40                  45

Asn Tyr Lys Asn His Val Arg Ile His Thr Gly Glu Lys Pro Tyr Val
    50                  55                  60

Cys Thr Val Pro Gly Cys Asp Lys Arg Phe Thr Glu Tyr Ser Ser Leu
65              70                  75                  80

Tyr Lys His His Val Val His Thr His Ser
                85                  90

```
<210> SEQ ID NO 5
<211> LENGTH: 96
<212> TYPE: PRT
<213> ORGANISM: Mus musculus
<220> FEATURE:
<221> NAME/KEY: ZN_FING
<222> LOCATION: (1)...(96)

<400> SEQUENCE: 5
```

Lys Lys Glu Phe Val Cys Arg Trp Leu Asp Cys Ser Arg Glu Gln Lys
1               5                   10                  15

Pro Phe Lys Ala Gln Tyr Met Leu Val Val His Met Arg Arg His Thr
            20                  25                  30

Gly Glu Lys Pro His Lys Cys Thr Phe Glu Gly Cys Thr Lys Ala Tyr
        35                  40                  45

Ser Arg Leu Glu Asn Leu Lys Thr His Leu Arg Ser His Thr Gly Glu
    50                  55                  60

```
Lys Pro Tyr Val Cys Glu His Glu Gly Cys Asn Lys Ala Phe Ser Asn
 65                  70                  75                  80

Ala Ser Asp Arg Ala Lys His Gln Asn Arg Thr His Ser Asn Glu Lys
                 85                  90                  95

<210> SEQ ID NO 6
<211> LENGTH: 91
<212> TYPE: PRT
<213> ORGANISM: Homo sapiens
<220> FEATURE:
<221> NAME/KEY: ZN_FING
<222> LOCATION: (1)...(91)

<400> SEQUENCE: 6

Glu Arg Pro Phe Lys Cys Pro Phe Glu Gly Cys Gly Arg Ser Phe Thr
 1               5                  10                  15

Thr Ser Asn Ile Arg Lys Val His Val Arg Thr His Thr Gly Glu Arg
                20                  25                  30

Pro Tyr Tyr Cys Thr Glu Pro Gly Cys Gly Arg Ala Phe Ala Ser Ala
             35                  40                  45

Thr Asn Tyr Lys Asn His Val Arg Ile His Thr Gly Glu Lys Pro Tyr
         50                  55                  60

Val Cys Thr Val Pro Gly Cys Asp Lys Arg Phe Thr Glu Tyr Ser Ser
 65                  70                  75                  80

Leu Tyr Lys His His Val Val His Thr His Ser
                 85                  90

<210> SEQ ID NO 7
<211> LENGTH: 53
<212> TYPE: PRT
<213> ORGANISM: Saccharomyces cerevisiae
<220> FEATURE:
<221> NAME/KEY: ZN_FING
<222> LOCATION: (1)...(53)

<400> SEQUENCE: 7

Gly Lys Asn Lys Ile Tyr Ile Cys Lys Glu Cys Gln Arg Lys Phe Ser
 1               5                  10                  15

Ser Gly His His Leu Thr Arg His Lys Lys Ser Val His Ser Gly Glu
                20                  25                  30

Lys Pro His Ser Cys Pro Lys Cys Gly Lys Arg Phe Lys Arg Arg Asp
             35                  40                  45

His Val Leu Gln His
         50

<210> SEQ ID NO 8
<211> LENGTH: 397
<212> TYPE: PRT
<213> ORGANISM: Arabidopsis thaliana

<400> SEQUENCE: 8

Met Ala Val Ser Glu Gln Ser Gln Asp Val Phe Pro Trp Leu Lys Ser
 1               5                  10                  15

Leu Pro Val Ala Pro Glu Phe Arg Pro Thr Leu Ala Glu Phe Gln Asp
                20                  25                  30

Pro Ile Ala Tyr Ile Leu Lys Ile Glu Glu Ala Ser Arg Tyr Gly
             35                  40                  45

Ile Cys Lys Ile Leu Pro Pro Leu Pro Pro Ser Lys Lys Thr Ser
         50                  55                  60

Ile Ser Asn Leu Asn Arg Ser Leu Ala Ala Arg Ala Ala Ala Arg Val
```

-continued

```
            65                  70                  75                  80
Arg Asp Gly Gly Phe Gly Ala Cys Asp Tyr Asp Gly Pro Thr Phe
                    85                  90                  95
Ala Thr Arg Gln Gln Gln Ile Gly Phe Cys Pro Arg Lys Gln Arg Pro
                100                 105                 110
Val Gln Arg Pro Val Trp Gln Ser Gly Glu Glu Tyr Ser Phe Gly Glu
            115                 120                 125
Phe Glu Phe Lys Ala Lys Asn Phe Glu Lys Asn Tyr Leu Lys Lys Cys
        130                 135                 140
Gly Lys Lys Ser Gln Leu Ser Ala Leu Glu Ile Glu Thr Leu Tyr Trp
145                 150                 155                 160
Arg Ala Thr Val Asp Lys Pro Phe Ser Val Glu Tyr Ala Asn Asp Met
                165                 170                 175
Pro Gly Ser Ala Phe Ile Pro Leu Ser Leu Ala Ala Arg Arg Arg
                180                 185                 190
Glu Ser Gly Gly Gly Gly Thr Val Gly Glu Thr Ala Trp Asn Met
            195                 200                 205
Arg Ala Met Ser Arg Ala Glu Gly Ser Leu Leu Lys Phe Met Lys Glu
        210                 215                 220
Glu Ile Pro Gly Val Thr Ser Pro Met Val Tyr Val Ala Met Met Phe
225                 230                 235                 240
Ser Trp Phe Ala Trp His Val Glu Asp His Asp Leu His Ser Leu Asn
                245                 250                 255
Tyr Leu His Met Gly Ala Gly Lys Thr Trp Tyr Gly Val Pro Lys Asp
                260                 265                 270
Ala Ala Leu Ala Phe Glu Glu Val Val Arg Val His Gly Tyr Gly Glu
            275                 280                 285
Glu Leu Asn Pro Leu Val Thr Phe Ser Thr Leu Gly Glu Lys Thr Thr
        290                 295                 300
Val Met Ser Pro Glu Val Phe Val Lys Ala Gly Ile Pro Cys Cys Arg
305                 310                 315                 320
Leu Val Gln Asn Pro Gly Glu Phe Val Val Thr Phe Pro Gly Ala Tyr
                325                 330                 335
His Ser Gly Phe Ser His Gly Phe Asn Phe Gly Glu Ala Ser Asn Ile
                340                 345                 350
Ala Thr Pro Glu Trp Leu Arg Met Ala Lys Asp Ala Ala Ile Arg Arg
            355                 360                 365
Ala Ala Ile Asn Tyr Pro Pro Met Val Ser His Leu Gln Leu Leu Tyr
        370                 375                 380
Asp Phe Val Leu Ala Leu Gly Ser Arg Val Pro Thr Ser
385                 390                 395

<210> SEQ ID NO 9
<211> LENGTH: 301
<212> TYPE: PRT
<213> ORGANISM: Homo sapiens

<400> SEQUENCE: 9

Pro Glu Cys Pro Val Phe Glu Pro Ser Trp Glu Glu Phe Thr Asp Pro
1               5                   10                  15
Leu Ser Phe Ile Gly Arg Ile Arg Pro Leu Ala Glu Lys Thr Gly Ile
                20                  25                  30
Cys Lys Ile Arg Pro Pro Gln Ala Val Arg Glu Tyr Thr Leu Gln Ser
            35                  40                  45
```

-continued

```
Phe Gly Glu Met Ala Asp Asn Phe Lys Ser Asp Tyr Phe Asn Met Pro
     50                  55                  60

Val His Met Val Pro Thr Glu Leu Val Glu Lys Glu Phe Trp Arg Leu
 65                  70                  75                  80

Val Ser Ser Ile Glu Glu Asp Val Ile Val Glu Tyr Gly Ala Asp Ile
                 85                  90                  95

Ser Ser Lys Asp Phe Gly Ser Gly Phe Pro Val Lys Asp Gly Arg Arg
             100                 105                 110

Lys Ile Leu Pro Glu Glu Glu Tyr Ala Leu Ser Gly Trp Asn Leu
             115                 120                 125

Asn Asn Met Pro Val Leu Glu Gln Ser Val Leu Ala His Ile Asn Val
     130                 135                 140

Asp Ile Ser Gly Met Lys Val Pro Trp Leu Tyr Val Gly Met Cys Phe
145                 150                 155                 160

Ser Ser Phe Cys Trp His Ile Glu Asp His Trp Ser Tyr Ser Ile Asn
                 165                 170                 175

Tyr Leu His Trp Gly Glu Pro Lys Thr Trp Tyr Gly Val Pro Ser His
             180                 185                 190

Ala Ala Glu Gln Leu Glu Val Met Arg Glu Leu Ala Pro Glu Leu
             195                 200                 205

Phe Glu Ser Gln Pro Asp Leu Leu His Gln Leu Val Thr Ile Met Asn
     210                 215                 220

Pro Asn Val Leu Met Glu His Gly Val Pro Val Tyr Arg Thr Asn Gln
225                 230                 235                 240

Cys Ala Gly Glu Phe Val Thr Phe Pro Arg Ala Tyr His Ser Gly
                 245                 250                 255

Phe Asn Gln Gly Tyr Asn Phe Ala Glu Ala Val Asn Phe Cys Thr Ala
             260                 265                 270

Asp Trp Leu Pro Ile Gly Arg Gln Cys Val Asn His Tyr Arg Arg Leu
     275                 280                 285

Arg Arg His Cys Val Phe Ser His Glu Glu Leu Ile Phe
290                 295                 300
```

<210> SEQ ID NO 10
<211> LENGTH: 301
<212> TYPE: PRT
<213> ORGANISM: Mus musculus

<400> SEQUENCE: 10

```
Pro Glu Cys Pro Val Phe Glu Pro Ser Trp Ala Glu Phe Arg Asp Pro
 1               5                  10                  15

Leu Gly Tyr Ile Ala Lys Ile Arg Pro Ile Ala Glu Lys Ser Gly Ile
                 20                  25                  30

Cys Lys Ile Arg Pro Pro Gln Ala Thr Arg Glu Tyr Thr Leu Gln Ser
             35                  40                  45

Phe Gly Glu Met Ala Asp Ser Phe Lys Ala Asp Tyr Phe Asn Met Pro
     50                  55                  60

Val His Met Val Pro Thr Glu Leu Val Glu Lys Glu Phe Trp Arg Leu
 65                  70                  75                  80

Val Asn Ser Ile Glu Glu Asp Val Thr Val Glu Tyr Gly Ala Asp Ile
                 85                  90                  95

His Ser Lys Glu Phe Gly Ser Gly Phe Pro Val Ser Asp Ser Lys Arg
             100                 105                 110

His Leu Thr Pro Glu Glu Glu Tyr Ala Thr Ser Gly Trp Asn Leu
             115                 120                 125
```

```
Asn Val Met Pro Val Leu Glu Gln Ser Val Leu Cys His Ile Asn Ala
            130                 135                 140

Asp Ile Ser Gly Met Lys Val Pro Trp Leu Tyr Val Gly Met Val Phe
145                 150                 155                 160

Ser Ala Phe Cys Trp His Ile Glu Asp His Trp Ser Tyr Ser Ile Asn
                165                 170                 175

Tyr Leu His Trp Gly Glu Pro Lys Thr Trp Tyr Gly Val Pro Ser Leu
            180                 185                 190

Ala Ala Glu His Leu Glu Val Met Lys Lys Leu Thr Pro Glu Leu
            195                 200                 205

Phe Asp Ser Gln Pro Asp Leu Leu His Gln Leu Val Thr Leu Met Asn
    210                 215                 220

Pro Asn Thr Leu Met Ser His Gly Val Pro Val Val Arg Thr Asn Gln
225                 230                 235                 240

Cys Ala Gly Glu Phe Val Ile Thr Phe Pro Arg Ala Tyr His Ser Gly
                245                 250                 255

Phe Asn Gln Gly Tyr Asn Phe Ala Glu Ala Val Asn Phe Cys Thr Ala
            260                 265                 270

Asp Trp Leu Pro Ala Gly Arg Gln Cys Ile Glu His Tyr Arg Arg Leu
            275                 280                 285

Arg Arg Tyr Cys Val Phe Ser His Glu Glu Leu Ile Cys
            290                 295                 300

<210> SEQ ID NO 11
<211> LENGTH: 304
<212> TYPE: PRT
<213> ORGANISM: Drosophila melanogaster

<400> SEQUENCE: 11

Pro Glu Cys Pro Val Phe Arg Pro Thr Thr Glu Glu Phe Lys Asn Pro
1               5                   10                  15

Leu Ala Tyr Ile Ser Lys Ile Arg Ser Ile Ala Glu Lys Cys Gly Ile
            20                  25                  30

Ala Lys Ile Leu Pro Pro Gln Ala Glu Arg Glu Tyr Thr Leu Gln Gln
        35                  40                  45

Phe Gly Gln Met Ala Asp Gln Phe Lys Gln Glu Tyr Phe Arg Lys Pro
50                  55                  60

Val His Leu Val Pro Thr Glu Met Val Glu Arg Glu Phe Trp Arg Ile
65                  70                  75                  80

Val Ser Ser Ile Asp Glu Asp Val Thr Val Glu Tyr Gly Ala Asp Leu
                85                  90                  95

His Thr Met Asp His Gly Ser Gly Phe Pro Thr Lys Ser Ser Leu Tyr
            100                 105                 110

Leu Leu Pro Gly Asp Gln Glu Tyr Ala Glu Ser Ser Trp Asn Leu Asn
        115                 120                 125

Asn Leu Pro Leu Leu Glu Asp Ser Ile Leu Gly His Ile Asn Ala Asp
    130                 135                 140

Ile Ser Gly Met Asn Ala Pro Trp Met Tyr Val Gly Met Cys Phe Ala
145                 150                 155                 160

Ala Phe Cys Trp His Asn Glu Asp His Trp Ser Tyr Ser Ile Asn Tyr
                165                 170                 175

Leu His Trp Gly Glu Pro Lys Thr Trp Tyr Gly Val Pro Gly Ser Cys
            180                 185                 190

Ala Glu Gln Phe Glu Glu Thr Met Lys Gln Ala Ala Pro Glu Leu Phe
```

```
                195                 200                 205
Ser Ser Gln Pro Asp Leu Leu His Gln Leu Val Thr Ile Met Asn Pro
    210                 215                 220

Asn Ile Leu Met Asn Asn Arg Val Pro Val Phe Arg Thr Asp Gln His
225                 230                 235                 240

Ala Gly Glu Phe Val Ile Thr Phe Pro Arg Ala Tyr His Ala Gly Phe
                245                 250                 255

Asn Gln Gly Tyr Asn Phe Ala Glu Ala Val Asn Phe Ala Pro Ala Asp
                260                 265                 270

Trp Leu Lys Met Gly Arg Glu Cys Val Asn His Tyr Ser Met Leu Arg
            275                 280                 285

Arg Phe Cys Val Phe Ser His Asp Glu Leu Val Cys Lys Met Ala Leu
    290                 295                 300

<210> SEQ ID NO 12
<211> LENGTH: 317
<212> TYPE: PRT
<213> ORGANISM: Schizosaccharomyces pombe

<400> SEQUENCE: 12

Ile His Gly Leu Pro Val Ala Pro Val Phe Tyr Pro Asp Lys Glu Glu
1               5                   10                  15

Phe Gln Asp Ser Ile Gly Tyr Ile Asn Lys Ile Ala Pro Ile Gly Glu
                20                  25                  30

Lys Tyr Gly Ile Ile Lys Ile Val Pro Pro Phe Glu Thr Gly Asn Tyr
            35                  40                  45

Tyr Thr Leu Ser Asn Phe Glu Lys Tyr Cys Asp Asn Phe Lys Lys Asn
        50                  55                  60

Tyr Phe Ser Lys Phe Lys Asp Ser Glu Ile Thr Glu Asp Ile Val Glu
65                  70                  75                  80

Lys Glu Tyr Trp Lys Leu Val Lys Asp Asn Asn Thr Ser Leu Glu Val
                85                  90                  95

Glu Tyr Gly Ala Asp Leu Ser Thr Leu Asp Gln Gly Ser Ala Phe Pro
            100                 105                 110

Ser Leu Ala Lys Asn Pro Val Asn Pro Tyr Ser Lys Asp Thr Trp Asn
        115                 120                 125

Leu Asn Val Ile Ala Ser Thr Asn Gly Ser Leu Leu Ser Tyr Ile Asp
    130                 135                 140

Asn Pro Val Ser Gly Ile Thr Cys Pro Trp Leu Tyr Val Gly Met Cys
145                 150                 155                 160

Phe Ser Thr Phe Cys Trp His Val Glu Asp Asn Tyr Thr Tyr Ser Val
                165                 170                 175

Asn Tyr Gln His Tyr Gly Asp Thr Lys Leu Trp Tyr Gly Ile Pro Gly
            180                 185                 190

Asp Gln Ala Glu Arg Phe Glu Arg Ala Leu Asp Ile Ala Pro Asp
        195                 200                 205

Leu Val Lys Lys Gln Lys Asp Leu Leu Tyr Gln Leu Ala Thr Met Ile
    210                 215                 220

Asn Pro Asp Glu Leu Gln Lys Arg Gly Val Asp Val Tyr Phe Ile Asp
225                 230                 235                 240

Gln Gly Pro Asn Glu Phe Val Ile Thr Phe Pro Lys Ser Phe His Ala
                245                 250                 255

Gly Ile Asn His Gly Phe Asn Ile Asn Glu Ala Val Asn Phe Ala Pro
            260                 265                 270
```

```
Lys Asp Trp Leu Leu Asn Gly Phe Ser Leu Asn Gly Val Leu Lys Tyr
            275                 280                 285

Gln Ser Leu Leu Lys Pro Pro Val Leu Ser His Asp Met Leu Val Tyr
        290                 295                 300

Asn Leu Ala Thr Asn Pro Ala Ser Glu Ile Ser Val Ser
305                 310                 315

<210> SEQ ID NO 13
<211> LENGTH: 313
<212> TYPE: PRT
<213> ORGANISM: Arabidopsis thaliana

<400> SEQUENCE: 13

Asn Val Pro Leu Gly Pro Val Tyr Tyr Pro Thr Glu Asp Glu Phe Lys
1               5                   10                  15

Asp Pro Leu Glu Tyr Ile His Lys Ile Lys Pro Glu Ala Glu Val Tyr
            20                  25                  30

Gly Ile Cys Lys Ile Val Pro Pro Val Ser Arg Thr Gln Ile Glu Lys
        35                  40                  45

Lys Phe Trp Glu Ile Val Glu Gly Ser Gly Glu Val Glu Val Met
50                  55                  60

Tyr Gly Asn Asp Leu Asp Thr Ser Val Tyr Gly Ser Gly Phe Pro Arg
65                  70                  75                  80

Ile Gly Asp Gln Arg Pro Glu Ser Val Glu Ala Asp Ile Trp Asp Glu
                85                  90                  95

Tyr Cys Gly Ser Pro Trp Asn Leu Asn Asn Met Pro Lys Leu Lys Gly
            100                 105                 110

Ser Met Leu Gln Ala Ile Arg His Asn Ile Asn Gly Val Thr Val Pro
        115                 120                 125

Trp Leu Tyr Leu Gly Met Leu Phe Ser Ser Phe Cys Trp His Phe Glu
130                 135                 140

Asp His Cys Phe Tyr Ser Val Asn Tyr Leu His Trp Gly Glu Ala Lys
145                 150                 155                 160

Cys Trp Tyr Gly Ile Pro Gly Ser Ala Ala Ser Ala Phe Glu Lys Val
                165                 170                 175

Met Arg Lys Thr Leu Pro Asp Leu Phe Asp Ala Gln Pro Asp Leu Leu
            180                 185                 190

Phe Gln Leu Val Thr Met Leu Ser Pro Thr Val Leu Gln Glu Asn Lys
        195                 200                 205

Val Pro Val Tyr Thr Val Leu Gln Glu Pro Gly Asn Phe Val Ile Thr
    210                 215                 220

Phe Pro Lys Ser Phe His Ala Gly Phe Asn Phe Gly Leu Asn Cys Ala
225                 230                 235                 240

Glu Ala Val Asn Phe Ala Thr Ala Asp Trp Leu Pro Tyr Gly Gly Ser
                245                 250                 255

Gly Ala Glu Leu Tyr Arg Leu Tyr Arg Lys Pro Ser Val Ile Ser His
            260                 265                 270

Glu Glu Leu Leu Cys Val Val Ala Lys Gly Asn Cys Cys Asn Asn Glu
        275                 280                 285

Gly Ser Ile His Leu Lys Lys Glu Leu Leu Arg Ile Tyr Ser Lys Glu
    290                 295                 300

Lys Thr Trp Arg Glu Gln Leu Trp Lys
305                 310

<210> SEQ ID NO 14
```

<211> LENGTH: 366
<212> TYPE: PRT
<213> ORGANISM: Arabidopsis thaliana

<400> SEQUENCE: 14

```
Met Ala Val Ser Glu Gln Ser Gln Asp Val Phe Pro Trp Leu Lys Ser
  1               5                  10                  15

Leu Pro Val Ala Pro Glu Phe Arg Pro Thr Leu Ala Glu Phe Gln Asp
             20                  25                  30

Pro Ile Ala Tyr Ile Leu Lys Ile Glu Glu Ala Ser Arg Tyr Gly
         35                  40                  45

Ile Cys Lys Ile Leu Pro Pro Leu Pro Pro Ser Lys Lys Thr Ser
 50                  55                  60

Ile Ser Asn Leu Asn Arg Ser Leu Ala Ala Arg Ala Ala Arg Val
 65                  70                  75                  80

Arg Asp Gly Gly Phe Gly Ala Cys Asp Tyr Asp Gly Pro Thr Phe
                 85                  90                  95

Ala Thr Arg Gln Gln Gln Ile Gly Phe Cys Pro Arg Lys Gln Arg Pro
                100                 105                 110

Val Gln Arg Pro Val Trp Gln Ser Gly Glu Glu Tyr Ser Phe Gly Glu
            115                 120                 125

Phe Glu Phe Lys Ala Lys Asn Phe Glu Lys Asn Tyr Leu Lys Lys Cys
130                 135                 140

Gly Lys Lys Ser Gln Leu Ser Ala Leu Glu Ile Glu Thr Leu Tyr Trp
145                 150                 155                 160

Arg Ala Thr Val Asp Lys Pro Phe Ser Val Glu Tyr Ala Asn Asp Met
                165                 170                 175

Pro Gly Ser Ala Phe Ile Pro Leu Ser Leu Ala Ala Arg Arg Arg
            180                 185                 190

Glu Ser Gly Gly Glu Gly Gly Thr Val Gly Glu Thr Ala Trp Asn Met
            195                 200                 205

Arg Ala Met Ser Arg Ala Glu Gly Ser Leu Leu Lys Phe Met Lys Glu
210                 215                 220

Glu Ile Pro Gly Val Thr Ser Pro Met Val Tyr Val Ala Met Met Phe
225                 230                 235                 240

Ser Trp Phe Ala Trp His Val Glu Asp His Asp Leu His Ser Leu Asn
                245                 250                 255

Tyr Leu His Met Gly Ala Gly Lys Thr Trp Tyr Gly Val Pro Lys Asp
            260                 265                 270

Ala Ala Leu Ala Phe Glu Glu Val Arg Val His Gly Tyr Gly Glu
275                 280                 285

Glu Leu Asn Pro Leu Val Thr Phe Ser Thr Leu Gly Glu Lys Thr Thr
            290                 295                 300

Val Met Ser Pro Glu Val Phe Val Lys Ala Gly Ile Pro Cys Cys Arg
305                 310                 315                 320

Leu Val Gln Asn Pro Gly Glu Phe Val Val Thr Phe Pro Gly Ala Tyr
                325                 330                 335

His Ser Gly Phe Ser His Gly Phe Asn Phe Gly Glu Ala Ser Asn Ile
            340                 345                 350

Ala Thr Pro Glu Trp Leu Arg Met Ala Lys Asp Ala Ala Ile
            355                 360                 365
```

<210> SEQ ID NO 15
<211> LENGTH: 336
<212> TYPE: PRT

<213> ORGANISM: Saccharomyces cerevisiae

<400> SEQUENCE: 15

| | | | | | | | | | | | | | | |
|---|---|---|---|---|---|---|---|---|---|---|---|---|---|---|
| Pro | Val | Phe | Lys | Pro | Thr | Tyr | Glu | Gln | Phe | Glu | Asp | Phe | Tyr | Ala | Tyr |
| 1 | | | | 5 | | | | | 10 | | | | | 15 | |
| Cys | Lys | Ala | Ile | Asn | Lys | Tyr | Gly | Met | Lys | Ser | Gly | Val | Val | Lys | Val |
| | | | 20 | | | | | 25 | | | | | 30 | | |
| Ile | Pro | Pro | Lys | Glu | Trp | Lys | Asp | Lys | Leu | Asp | Leu | Pro | Tyr | Ser | Ala |
| | | 35 | | | | | 40 | | | | | 45 | | | |
| Glu | Thr | Leu | Gln | Lys | Ile | Lys | Ile | Lys | Ser | Pro | Ile | Gln | Gln | His | Ile |
| | 50 | | | | | 55 | | | | | 60 | | | | |
| Ser | Gly | Asn | Lys | Gly | Leu | Phe | Met | Val | Gln | Asn | Val | Glu | Lys | Asn | Lys |
| 65 | | | | | 70 | | | | | 75 | | | | | 80 |
| Thr | Tyr | Asn | Ile | Ile | Gln | Trp | Lys | Asp | Leu | Ser | Lys | Asp | Tyr | Val | Pro |
| | | | | 85 | | | | | 90 | | | | | 95 | |
| Pro | Glu | Asp | Pro | Lys | Ala | Arg | Arg | Asn | Ser | Arg | Lys | Gly | Ser | Val | Ser |
| | | | 100 | | | | | 105 | | | | | 110 | | |
| Lys | Ser | Thr | Lys | Leu | Lys | Leu | Lys | Asn | Phe | Glu | Ser | Ser | Phe | Asn | Ile |
| | | 115 | | | | | 120 | | | | | 125 | | | |
| Asp | Asp | Phe | Glu | Gln | Phe | Arg | Thr | Glu | Tyr | Thr | Ile | Asp | Leu | Ser | Asp |
| | 130 | | | | | 135 | | | | | 140 | | | | |
| Phe | Gln | Asn | Thr | Glu | Arg | Leu | Lys | Phe | Leu | Glu | Glu | Tyr | Tyr | Trp | Lys |
| 145 | | | | | 150 | | | | | 155 | | | | | 160 |
| Thr | Leu | Asn | Phe | Thr | Thr | Pro | Met | Tyr | Gly | Ala | Asp | Thr | Pro | Gly | Ser |
| | | | | 165 | | | | | 170 | | | | | 175 | |
| Ile | Phe | Pro | Glu | Gly | Leu | Asn | Val | Trp | Asn | Val | Ala | Lys | Leu | Pro | Asn |
| | | | 180 | | | | | 185 | | | | | 190 | | |
| Ile | Leu | Asp | His | Met | Glu | Thr | Lys | Val | Pro | Gly | Val | Asn | Asp | Ser | Tyr |
| | | 195 | | | | | 200 | | | | | 205 | | | |
| Leu | Tyr | Ala | Gly | Leu | Trp | Lys | Ala | Ser | Phe | Ser | Trp | His | Leu | Glu | Asp |
| | 210 | | | | | 215 | | | | | 220 | | | | |
| Gln | Asp | Leu | Tyr | Ser | Ile | Asn | Tyr | Ile | His | Phe | Gly | Ala | Pro | Lys | Gln |
| 225 | | | | | 230 | | | | | 235 | | | | | 240 |
| Trp | Tyr | Ser | Ile | Pro | Gln | Glu | Asp | Arg | Phe | Lys | Phe | Tyr | Lys | Phe | Met |
| | | | | 245 | | | | | 250 | | | | | 255 | |
| Gln | Glu | Gln | Phe | Pro | Glu | Glu | Ala | Lys | Asn | Cys | Pro | Glu | Phe | Leu | Arg |
| | | | 260 | | | | | 265 | | | | | 270 | | |
| His | Lys | Met | Phe | Leu | Ala | Ser | Pro | Lys | Leu | Leu | Gln | Glu | Asn | Gly | Ile |
| | | 275 | | | | | 280 | | | | | 285 | | | |
| Arg | Cys | Asn | Glu | Ile | Val | His | His | Glu | Gly | Glu | Phe | Met | Ile | Thr | Tyr |
| | 290 | | | | | 295 | | | | | 300 | | | | |
| Pro | Tyr | Gly | Tyr | His | Ala | Gly | Phe | Asn | Tyr | Gly | Tyr | Asn | Leu | Ala | Glu |
| 305 | | | | | 310 | | | | | 315 | | | | | 320 |
| Ser | Val | Asn | Phe | Ala | Leu | Glu | Glu | Trp | Leu | Pro | Ile | Gly | Lys | Lys | Ala |
| | | | | 325 | | | | | 330 | | | | | 335 | |

<210> SEQ ID NO 16
<211> LENGTH: 362
<212> TYPE: PRT
<213> ORGANISM: Arabidopsis thaliana

<400> SEQUENCE: 16

| | | | | | | | | | | | | | | |
|---|---|---|---|---|---|---|---|---|---|---|---|---|---|---|---|
| Ala | Pro | Val | Phe | His | Pro | Thr | Ser | Glu | Glu | Phe | Glu | Asp | Thr | Leu | Ala |
| 1 | | | | 5 | | | | | 10 | | | | | 15 | |
| Tyr | Ile | Glu | Lys | Ile | Arg | Pro | Leu | Ala | Glu | Ser | Phe | Gly | Ile | Cys | Arg |

```
                 20                  25                  30
Ile Val Pro Pro Ser Asn Trp Ser Pro Pro Cys Arg Leu Lys Gly Asp
         35                  40                  45

Ser Ile Trp Lys Asn Lys Asn Phe Pro Thr Arg Val Gln Phe Val Asp
 50                  55                  60

Leu Leu Gln Asn Arg Gly Pro Val Lys Lys Thr Pro Lys Gly Arg
 65                  70                  75                  80

Lys Arg Lys Arg Gly Lys Tyr Ser Arg Thr Val Ala Pro Lys Lys Arg
                 85                  90                  95

Asn Gly Ser Val Ser Lys Ser Val Ser Thr Pro Lys Ala Thr Glu Glu
                100                 105                 110

Glu Asn Phe Gly Phe Glu Ser Gly Pro Glu Phe Thr Leu Glu Lys Phe
            115                 120                 125

Glu Lys Tyr Ala Gln Asp Phe Lys Asp Ser Tyr Phe Glu Arg Lys Asp
        130                 135                 140

Asn Val Gly Asp Pro Ser Val Glu Glu Ile Glu Gly Tyr Trp Arg
145                 150                 155                 160

Ile Ile Glu Lys Glu Thr Asn Glu Val Lys Val Leu Tyr Gly Thr Asp
                165                 170                 175

Leu Glu Asn Pro Ile Leu Gly Ser Gly Phe Ser Lys Gly Val Lys Ile
            180                 185                 190

Pro Thr Arg Arg Asn Asp Met Asp Lys Tyr Ile Ser Ser Gly Trp Asn
        195                 200                 205

Leu Asn Asn Leu Ala Arg Leu Gln Gly Ser Leu Leu Ser Phe Glu Asp
    210                 215                 220

Cys Glu Ile Ser Gly Val Gln Val Pro Trp Leu Tyr Val Gly Met Cys
225                 230                 235                 240

Phe Ser Thr Phe Cys Trp His Val Glu Asp Asn His Leu Tyr Ser Leu
                245                 250                 255

Asn Tyr His His Phe Gly Glu Pro Lys Val Trp Tyr Gly Val Pro Gly
            260                 265                 270

Ser His Ala Thr Gly Leu Glu Lys Ala Met Arg Lys His Leu Pro Asp
        275                 280                 285

Leu Phe Asp Glu Gln Pro Asp Leu Leu His Glu Leu Val Thr Gln Phe
    290                 295                 300

Ser Pro Thr Ile Leu Lys Asn Glu Gly Val Pro Val Tyr Arg Ala Val
305                 310                 315                 320

Gln Asn Ala Gly Glu Tyr Val Leu Thr Phe Pro Arg Ala Tyr His Ser
                325                 330                 335

Gly Phe Asn Cys Gly Phe Asn Cys Ala Glu Ala Val Asn Val Ala Pro
            340                 345                 350

Val Asp Trp Leu Ala His Gly Gln Asn Ala
        355                 360

<210> SEQ ID NO 17
<211> LENGTH: 300
<212> TYPE: PRT
<213> ORGANISM: Drosophila melanogaster

<400> SEQUENCE: 17

Lys Met Ser Glu Val Pro Arg Ile Lys Val Phe Arg Pro Thr Trp Glu
 1               5                  10                  15

Glu Phe Lys Asp Phe Pro Lys Tyr Val Ala Tyr Met Glu Ser Gln Gly
                20                  25                  30
```

```
Ala His Lys Ala Gly Leu Ala Lys Val Val Pro Pro Glu Trp Val
        35                  40                  45

Pro Arg Arg Ser Gly Tyr Ala Asp Leu Asp Ala Leu Asn Val Thr Ile
50                  55                  60

Pro Ala Pro Ile Cys Gln Val Val Thr Gly Lys Gln Gly Tyr Tyr Gln
65                      70                  75                  80

Gln Ile Asn Ile Gln Lys Lys Pro Leu Thr Val Lys Gln Phe Ser Glu
                85                  90                  95

Leu Ala Ser Thr Glu Arg Tyr Ala Thr Pro Lys His Phe Asp Phe Glu
            100                 105                 110

Asp Leu Glu Arg Lys Tyr Trp Lys Asn Ile Thr Tyr Val Ala Pro Ile
        115                 120                 125

Tyr Gly Ala Asp Val Ser Gly Ser Ile Thr Asp Thr Asp Gln Asp Ser
    130                 135                 140

Trp Asn Ile Asn Arg Leu Gly Thr Ile Leu Asp Tyr Val Asn Lys Asp
145                 150                 155                 160

Tyr Asn Ile Gln Ile Asp Gly Val Asn Thr Ala Tyr Leu Tyr Phe Gly
                165                 170                 175

Met Trp Lys Thr Thr Phe Ala Trp His Thr Glu Asp Met Asp Leu Tyr
            180                 185                 190

Ser Ile Asn Tyr Leu His Phe Gly Ala Pro Lys Thr Trp Tyr Val Val
        195                 200                 205

Pro Pro Glu Cys Gly Arg Lys Leu Glu Lys Val Ala Asn Gln Tyr Phe
    210                 215                 220

Pro Ala Ser Tyr Lys Asn Cys Asn Ala Tyr Leu Arg His Lys Met Thr
225                 230                 235                 240

Leu Ile Ser Pro Gln Ile Leu Lys Gln His Asp Val Pro Val Ser Lys
                245                 250                 255

Ile Thr Gln Glu Ala Gly Glu Ile Met Ile Thr Phe Pro Phe Gly Tyr
            260                 265                 270

His Ala Gly Phe Asn His Gly Phe Asn Cys Ala Glu Ser Thr Asn Phe
        275                 280                 285

Ala Met Glu Arg Trp Ile Glu Tyr Gly Lys Arg Ala
    290                 295                 300

<210> SEQ ID NO 18
<211> LENGTH: 295
<212> TYPE: PRT
<213> ORGANISM: Caenorhabditis elegans

<400> SEQUENCE: 18

Phe Tyr Pro Thr Met Arg Glu Phe Lys Asn Phe Ser Gln Tyr Ile Lys
1               5                   10                  15

Lys Ile Glu Gln Asn Gly Gly His Leu Lys Ala Gly Ile Ala Lys Ile
            20                  25                  30

Val Ala Pro Glu Gly Trp Thr Pro Arg Pro Thr Arg Lys Asp Phe Ser
        35                  40                  45

Asp Val Asp Asp Tyr Glu Ile Thr Gln Pro Ala Arg Glu Thr Ile Glu
    50                  55                  60

Ala Thr Glu Lys Pro Gly Ala Tyr Phe Lys Arg Asn Val Thr Cys Arg
65                  70                  75                  80

Arg Lys Met Pro Val Arg Glu Phe Arg Thr Leu Ala Asn Ser Ala Gln
                85                  90                  95

Tyr Arg Asn Pro Arg Pro Asp Leu Lys Gly Ser Glu Ile Glu Lys His
            100                 105                 110
```

```
Tyr Phe Asp Asn Ile Leu His Gly Glu Pro Ile Tyr Gly Ala Asp Thr
            115                 120                 125

Glu Gly Ser Phe Tyr Asp Ala Gln Val Glu Glu Trp Asn Met Asn Arg
    130                 135                 140

Leu Gly Thr Ile Leu Glu Asp Thr Asn Tyr Glu Ile Lys Gly Val Asn
145                 150                 155                 160

Thr Val Tyr Leu Tyr Phe Gly Met Tyr Lys Thr Thr Phe Pro Trp His
                165                 170                 175

Ala Glu Asp Met Asp Leu Ser Ile Asn Phe Leu His Phe Gly Ala Pro
            180                 185                 190

Lys Tyr Trp Phe Ala Ile Ser Ser Glu His Ala Asp Arg Phe Glu Arg
    195                 200                 205

Phe Met Ser Gln Gln Phe Ser Tyr Gln Asn Glu Tyr Ala Pro Gln Cys
    210                 215                 220

Lys Ala Phe Leu Arg His Lys Thr Tyr Leu Val Thr Pro Glu Leu Leu
225                 230                 235                 240

Arg Gln Ala Gly Ile Pro Tyr Ala Thr Met Val Gln Arg Pro Asn Glu
                245                 250                 255

Phe Ile Ile Thr Phe Pro Arg Gly Tyr His Met Gly Phe Asn Leu Gly
                260                 265                 270

Tyr Asn Leu Ala Glu Ser Thr Asn Phe Ala Ser Gln Arg Trp Ile Asp
            275                 280                 285

Tyr Gly Lys Asp Ala Val Leu
    290                 295

<210> SEQ ID NO 19
<211> LENGTH: 306
<212> TYPE: PRT
<213> ORGANISM: Homo sapiens

<400> SEQUENCE: 19

Met Glu Val Glu Val Glu Ser Pro Leu Asn Pro Ser Cys Lys Ile Met
1               5                   10                  15

Thr Phe Arg Pro Ser Met Glu Glu Phe Arg Glu Phe Asn Lys Tyr Leu
            20                  25                  30

Ala Tyr Met Glu Ser Lys Gly Ala His Arg Ala Gly Leu Ala Lys Val
        35                  40                  45

Ile Pro Pro Lys Glu Trp Lys Pro Arg Gln Cys Tyr Asp Asp Ile Asp
    50                  55                  60

Asn Leu Leu Ile Pro Ala Pro Ile Gln Gln Met Val Thr Gly Gln Ser
65                  70                  75                  80

Gly Leu Phe Thr Gln Tyr Asn Ile Gln Lys Lys Ala Met Thr Val Lys
                85                  90                  95

Glu Phe Arg Gln Leu Ala Asn Ser Gly Lys Tyr Cys Thr Pro Arg Tyr
            100                 105                 110

Leu Asp Tyr Glu Asp Leu Glu Arg Lys Tyr Trp Lys Asn Leu Thr Phe
        115                 120                 125

Val Ala Pro Ile Tyr Gly Ala Asp Ile Asn Gly Ser Ile Tyr Asp Glu
    130                 135                 140

Gly Val Asp Glu Trp Asn Ile Ala Arg Leu Asn Thr Val Leu Asp Val
145                 150                 155                 160

Val Glu Glu Glu Cys Gly Ile Ser Ile Glu Gly Val Asn Thr Pro Tyr
                165                 170                 175

Leu Tyr Phe Gly Met Trp Lys Thr Thr Phe Ala Trp His Thr Glu Asp
```

```
                        180                 185                 190
Met Asp Leu Tyr Ser Ile Asn Tyr Leu His Phe Gly Glu Pro Lys Ser
                195                 200                 205

Trp Tyr Ala Ile Pro Pro Glu His Gly Lys Arg Leu Glu Arg Leu Ala
            210                 215                 220

Gln Gly Phe Pro Ser Ser Gln Gly Cys Asp Ala Phe Leu Arg
225                 230                 235                 240

His Lys Met Thr Leu Ile Ser Pro Ser Val Lys Lys Tyr Gly Ile
                    245                 250                 255

Pro Phe Asp Lys Ile Thr Gln Glu Ala Gly Glu Phe Met Ile Thr Phe
                260                 265                 270

Pro Tyr Gly Tyr His Ala Gly Phe Asn His Gly Phe Asn Cys Ala Glu
                275                 280                 285

Ser Thr Asn Phe Ala Thr Val Arg Trp Ile Asp Tyr Gly Lys Val Ala
            290                 295                 300

Lys Leu
305

<210> SEQ ID NO 20
<211> LENGTH: 1359
<212> TYPE: PRT
<213> ORGANISM: Arabidopsis thaliana

<400> SEQUENCE: 20

Met Ala Val Ser Glu Gln Ser Gln Asp Val Phe Pro Trp Leu Lys Ser
1               5                   10                  15

Leu Pro Val Ala Pro Glu Phe Arg Pro Thr Leu Ala Glu Phe Gln Asp
                20                  25                  30

Pro Ile Ala Tyr Ile Leu Lys Ile Glu Glu Glu Ala Ser Arg Tyr Gly
            35                  40                  45

Ile Cys Lys Ile Leu Pro Pro Leu Pro Pro Pro Ser Lys Lys Thr Ser
50                  55                  60

Ile Ser Asn Leu Asn Arg Ser Leu Ala Ala Arg Ala Ala Ala Arg Val
65                  70                  75                  80

Arg Asp Gly Gly Phe Gly Ala Cys Asp Tyr Asp Gly Pro Thr Phe
                85                  90                  95

Ala Thr Arg Gln Gln Ile Gly Phe Cys Pro Arg Lys Gln Arg Pro
            100                 105                 110

Val Gln Arg Pro Val Trp Gln Ser Gly Glu Glu Tyr Ser Phe Gly Glu
            115                 120                 125

Phe Glu Phe Lys Ala Lys Asn Phe Glu Lys Asn Tyr Leu Lys Lys Cys
        130                 135                 140

Gly Lys Lys Ser Gln Leu Ser Ala Leu Glu Ile Glu Thr Leu Tyr Trp
145                 150                 155                 160

Arg Ala Thr Val Asp Lys Pro Phe Ser Val Glu Tyr Ala Asn Asp Met
                165                 170                 175

Pro Gly Ser Ala Phe Ile Pro Leu Ser Leu Ala Ala Arg Arg
            180                 185                 190

Glu Ser Gly Gly Glu Gly Gly Thr Val Gly Glu Thr Ala Trp Asn Met
        195                 200                 205

Arg Ala Met Ser Arg Ala Glu Gly Ser Leu Leu Lys Phe Met Lys Glu
        210                 215                 220

Glu Ile Pro Gly Val Thr Ser Pro Met Val Tyr Val Ala Met Met Phe
225                 230                 235                 240
```

-continued

```
Ser Trp Phe Ala Trp His Val Glu Asp His Asp Leu His Ser Leu Asn
            245                 250                 255
Tyr Leu His Met Gly Ala Gly Lys Thr Trp Tyr Gly Val Pro Lys Asp
            260                 265                 270
Ala Ala Leu Ala Phe Glu Glu Val Val Arg Val His Gly Tyr Gly Glu
            275                 280                 285
Glu Leu Asn Pro Leu Val Thr Phe Ser Thr Leu Gly Glu Lys Thr Thr
            290                 295                 300
Val Met Ser Pro Glu Val Phe Val Lys Ala Gly Ile Pro Cys Cys Arg
305                 310                 315                 320
Leu Val Gln Asn Pro Gly Glu Phe Val Thr Phe Pro Gly Ala Tyr
            325                 330                 335
His Ser Gly Phe Ser His Gly Phe Asn Phe Gly Glu Ala Ser Asn Ile
            340                 345                 350
Ala Thr Pro Glu Trp Leu Arg Met Ala Lys Asp Ala Ala Ile Arg Arg
            355                 360                 365
Ala Ala Ile Asn Tyr Pro Pro Met Val Ser His Leu Gln Leu Leu Tyr
370                 375                 380
Asp Phe Val Leu Ala Leu Gly Ser Arg Val Pro Thr Ser Ile Asn Pro
385                 390                 395                 400
Lys Pro Arg Ser Ser Arg Leu Lys Asp Lys Ala Arg Ser Glu Gly Glu
            405                 410                 415
Arg Leu Thr Lys Lys Leu Phe Val Gln Asn Ile Ile His Asn Asn Glu
            420                 425                 430
Leu Leu Ser Ser Leu Gly Lys Gly Ser Pro Val Ala Leu Leu Pro Gln
            435                 440                 445
Ser Ser Ser Asp Ile Ser Val Cys Ser Asp Leu Arg Ile Gly Ser His
            450                 455                 460
Leu Ile Thr Asn Gln Glu Asn Pro Ile Gln Leu Lys Cys Glu Asp Leu
465                 470                 475                 480
Ser Ser Asp Ser Val Val Asp Leu Ser Asn Gly Leu Lys Asp Thr
            485                 490                 495
Val Ser Val Lys Glu Lys Phe Thr Ser Leu Cys Glu Arg Ser Arg Asn
            500                 505                 510
His Leu Ala Ser Thr Glu Lys Asp Thr Gln Glu Thr Leu Ser Asp Ala
            515                 520                 525
Glu Arg Arg Lys Asn Asp Ala Ala Val Ala Leu Ser Asp Gln Arg Leu
            530                 535                 540
Phe Ser Cys Val Thr Cys Gly Val Leu Ser Phe Asp Cys Val Ala Ile
545                 550                 555                 560
Val Gln Pro Lys Glu Ala Ala Arg Tyr Leu Met Ser Ala Asp Cys
            565                 570                 575
Ser Phe Phe Asn Asp Trp Thr Ala Ala Ser Gly Ser Ala Asn Leu Gly
            580                 585                 590
Gln Ala Ala Arg Ser Leu His Pro Gln Ser Lys Glu Lys His Asp Val
            595                 600                 605
Asn Tyr Phe Tyr Asn Val Pro Val Gln Thr Met Asp His Ser Val Lys
            610                 615                 620
Thr Gly Asp Gln Lys Thr Ser Thr Thr Ser Pro Thr Ile Ala His Lys
625                 630                 635                 640
Asp Asn Asp Val Leu Gly Met Leu Ala Ser Ala Tyr Gly Asp Ser Ser
            645                 650                 655
Asp Ser Glu Glu Glu Asp Gln Lys Gly Leu Val Thr Pro Ser Ser Lys
```

-continued

```
            660                 665                 670
Gly Glu Thr Lys Thr Tyr Asp Gln Glu Gly Ser Asp Gly His Glu Glu
                675                 680                 685
Ala Arg Asp Gly Arg Thr Ser Asp Phe Asn Cys Gln Arg Leu Thr Ser
            690                 695                 700
Glu Gln Asn Gly Leu Ser Lys Gly Gly Lys Ser Ser Leu Leu Glu Ile
705                 710                 715                 720
Ala Leu Pro Phe Ile Pro Arg Ser Asp Asp Ser Cys Arg Leu His
                725                 730                 735
Val Phe Cys Leu Glu His Ala Ala Glu Val Glu Gln Gln Leu Arg Pro
                740                 745                 750
Phe Gly Gly Ile Asn Leu Met Leu Leu Cys His Pro Glu Tyr Pro Arg
                755                 760                 765
Ile Glu Ala Glu Ala Lys Ile Val Ala Glu Leu Val Ile Asn His
                770                 775                 780
Glu Trp Asn Asp Thr Glu Phe Arg Asn Val Thr Arg Glu Asp Glu Glu
785                 790                 795                 800
Thr Ile Gln Ala Ala Leu Asp Asn Val Glu Ala Lys Gly Gly Asn Ser
                805                 810                 815
Asp Trp Thr Val Lys Leu Gly Val Asn Leu Ser Tyr Ser Ala Ile Leu
                820                 825                 830
Ser Arg Ser Pro Leu Tyr Ser Lys Gln Met Pro Tyr Asn Ser Ile Ile
                835                 840                 845
Tyr Lys Ala Phe Gly Arg Ser Pro Val Ala Ser Pro Ser Lys
                850                 855                 860
Pro Lys Val Ser Gly Lys Arg Ser Ser Arg Gln Arg Lys Tyr Val Val
865                 870                 875                 880
Gly Lys Trp Cys Gly Lys Val Trp Met Ser His Gln Val His Pro Phe
                885                 890                 895
Leu Leu Glu Gln Asp Leu Glu Gly Glu Ser Glu Arg Ser Cys His
                900                 905                 910
Leu Arg Val Ala Met Asp Glu Asp Ala Thr Gly Lys Arg Ser Phe Pro
                915                 920                 925
Asn Asn Val Ser Arg Asp Ser Thr Thr Met Phe Gly Arg Lys Tyr Cys
930                 935                 940
Arg Lys Arg Lys Ile Arg Ala Lys Ala Val Pro Arg Lys Lys Leu Thr
945                 950                 955                 960
Ser Phe Lys Arg Glu Asp Gly Val Ser Asp Thr Ser Glu Asp His
                965                 970                 975
Ser Tyr Lys Gln Gln Trp Arg Ala Ser Gly Asn Glu Glu Ser Tyr
                980                 985                 990
Phe Glu Thr Gly Asn Thr Ala Ser Gly Asp Ser Ser Asn Gln Met Ser
                995                 1000                1005
Asp Pro His Lys Gly Ile Ile Arg His Lys Gly Tyr Lys Glu Phe Glu
                1010                1015                1020
Ser Asp Asp Glu Val Ser Asp Arg Ser Leu Gly Glu Glu Tyr Thr Val
1025                1030                1035                1040
Arg Ala Cys Ala Ala Ser Glu Ser Ser Met Glu Asn Gly Ser Gln His
                1045                1050                1055
Ser Met Tyr Asp His Asp Asp Asp Asp Ile Asp Arg Gln Pro
                1060                1065                1070
Arg Gly Ile Pro Arg Ser Gln Gln Thr Arg Val Phe Arg Asn Pro Val
                1075                1080                1085
```

-continued

Ser Tyr Glu Ser Glu Asp Asn Gly Val Tyr Gln Gln Ser Gly Arg Ile
    1090            1095                1100

Ser Ile Ser Asn Arg Gln Ala Asn Arg Met Val Gly Glu Tyr Asp Ser
1105            1110                1115                1120

Ala Glu Asn Ser Leu Glu Arg Gly Phe Cys Ser Thr Gly Lys Arg
            1125            1130                1135

Gln Thr Arg Ser Thr Ala Lys Arg Ile Ala Lys Thr Lys Thr Val Gln
            1140                1145                1150

Ser Ser Arg Asp Thr Lys Gly Arg Phe Leu Gln Glu Phe Ala Ser Gly
        1155            1160                1165

Lys Lys Asn Glu Glu Leu Asp Ser Tyr Met Glu Gly Pro Ser Thr Arg
    1170                1175            1180

Leu Arg Val Arg His Gln Lys Pro Ser Arg Gly Ser Leu Glu Thr Lys
1185                1190                1195                1200

Pro Lys Lys Ile Gly Lys Lys Arg Ser Gly Asn Ala Ser Phe Ser Arg
            1205                1210                1215

Val Ala Thr Glu Lys Asp Val Glu Glu Lys Glu Glu Glu Glu Glu
            1220                1225                1230

Glu Asn Glu Glu Glu Glu Cys Ala Ala Tyr Gln Cys Asn Met Glu Gly
        1235                1240                1245

Cys Thr Met Ser Phe Ser Ser Glu Lys Gln Leu Met Leu His Lys Arg
    1250                1255            1260

Asn Ile Cys Pro Ile Lys Gly Cys Gly Lys Asn Phe Phe Ser His Lys
1265                1270                1275                1280

Tyr Leu Val Gln His Gln Arg Val His Ser Asp Asp Arg Pro Leu Lys
            1285                1290                1295

Cys Pro Trp Lys Gly Cys Lys Met Thr Phe Lys Trp Ala Trp Ser Arg
        1300                1305                1310

Thr Glu His Ile Arg Val His Thr Gly Ala Arg Pro Tyr Val Cys Ala
    1315                1320                1325

Glu Pro Asp Cys Gly Gln Thr Phe Arg Phe Val Ser Asp Phe Ser Arg
    1330                1335                1340

His Lys Arg Lys Thr Gly His Ser Val Lys Lys Thr Asn Lys Arg
1345            1350                1355

<210> SEQ ID NO 21
<211> LENGTH: 476
<212> TYPE: PRT
<213> ORGANISM: Arabidopsis thaliana
<220> FEATURE:
<221> NAME/KEY: VARSPLIC
<222> LOCATION: (1)...(476)

<400> SEQUENCE: 21

Met Ala Val Ser Glu Gln Ser Gln Asp Val Phe Pro Trp Leu Lys Ser
1               5                   10                  15

Leu Pro Val Ala Pro Glu Phe Arg Pro Thr Leu Ala Glu Phe Gln Asp
            20                  25                  30

Pro Ile Ala Tyr Ile Leu Lys Ile Glu Glu Ala Ser Arg Tyr Gly
        35                  40                  45

Ile Cys Lys Ile Leu Pro Pro Leu Pro Pro Ser Lys Lys Thr Ser
    50                  55                  60

Ile Ser Asn Leu Asn Arg Ser Leu Ala Ala Arg Ala Ala Arg Val
65              70                  75                  80

Arg Asp Gly Gly Phe Gly Ala Cys Asp Tyr Asp Gly Gly Pro Thr Phe

```
                85                  90                  95
Ala Thr Arg Gln Gln Ile Gly Phe Cys Pro Arg Lys Gln Arg Pro
               100                 105                 110
Val Gln Arg Pro Val Trp Gln Ser Gly Glu Glu Tyr Ser Phe Gly Glu
               115                 120                 125
Phe Glu Phe Lys Ala Lys Asn Phe Glu Lys Asn Tyr Leu Lys Lys Cys
               130                 135                 140
Gly Lys Lys Ser Gln Leu Ser Ala Leu Glu Ile Glu Thr Leu Tyr Trp
145                 150                 155                 160
Arg Ala Thr Val Asp Lys Pro Phe Ser Val Glu Tyr Ala Asn Asp Met
                    165                 170                 175
Pro Gly Ser Ala Phe Ile Pro Leu Ser Leu Ala Ala Arg Arg
                    180                 185                 190
Glu Ser Gly Gly Glu Gly Gly Thr Val Gly Glu Thr Ala Trp Asn Met
                    195                 200                 205
Arg Ala Met Ser Arg Ala Glu Gly Ser Leu Leu Lys Phe Met Lys Glu
                    210                 215                 220
Glu Ile Pro Gly Val Thr Ser Pro Met Val Tyr Val Ala Met Met Phe
225                 230                 235                 240
Ser Trp Phe Ala Trp His Val Glu Asp His Asp Leu His Ser Leu Asn
                    245                 250                 255
Tyr Leu His Met Gly Ala Gly Lys Thr Trp Tyr Gly Val Pro Lys Asp
                    260                 265                 270
Ala Ala Leu Ala Phe Glu Glu Val Val Arg Val His Gly Tyr Gly Glu
                    275                 280                 285
Glu Leu Asn Pro Leu Val Thr Phe Ser Thr Leu Gly Glu Lys Thr Thr
                    290                 295                 300
Val Met Ser Pro Glu Val Phe Val Lys Ala Gly Ile Pro Cys Cys Arg
305                 310                 315                 320
Leu Val Gln Asn Pro Gly Glu Phe Val Thr Phe Pro Gly Ala Tyr
                    325                 330                 335
His Ser Gly Phe Ser His Gly Phe Asn Phe Gly Glu Ala Ser Asn Ile
                    340                 345                 350
Ala Thr Pro Glu Trp Leu Arg Met Ala Lys Asp Ala Ala Ile Arg Arg
                    355                 360                 365
Ala Ala Ile Asn Tyr Pro Pro Met Val Ser His Leu Gln Leu Leu Tyr
                    370                 375                 380
Asp Phe Val Leu Ala Leu Gly Ser Arg Val Pro Thr Ser Ile Asn Pro
385                 390                 395                 400
Lys Pro Arg Ser Ser Arg Leu Lys Asp Lys Ala Arg Ser Glu Gly Glu
                    405                 410                 415
Arg Leu Thr Lys Lys Leu Phe Val Gln Asn Ile Ile His Asn Asn Glu
                    420                 425                 430
Leu Leu Ser Ser Leu Gly Lys Gly Ser Pro Val Ala Leu Leu Pro Gln
                    435                 440                 445
Ser Ser Ser Asp Ile Ser Val Cys Ser Asp Leu Arg Ile Gly Ser His
                    450                 455                 460
Leu Ile Thr Asn Gln Glu Asn Pro Ile Gln Leu Lys
465                 470                 475

<210> SEQ ID NO 22
<211> LENGTH: 4575
<212> TYPE: DNA
<213> ORGANISM: Arabidopsis thaliana
```

```
<400> SEQUENCE: 22
cagagagacc taagaaacga gatcaacaaa gcccgtcgtt tttttcgagg aaaagtgaat      60
gacccttTaa gaaataact ctattggccg gagaaatggt ggagactcgt cgattctctt     120
aaagtttgtt tttttttcct ctcttcaaaa tttttgttct gtttatactc tgtaatggcg     180
ttttaatttg atacctagaa gttaaagtga acaaattttg agagaaagtc tctttttttt     240
gttcttccct gtgtgtgtga gagagagaga gatatggcgg tttcagagca gagtcaagat     300
gtgtttccat ggcttaaatc gttaccggtt gctccagagt tcagacctac tctagcagag     360
tttcaagatc cgatcgctta cattttgaag attgaagaag aagcttctag atatggaatc     420
tgtaaaattc tgcctccact gcctcctcct tccaaaaaaa cctcgatttc taatctcaac     480
cgttctctgg cggcaagagc ggcggcgagg gttcgtgacg gcggctttgg cgcgtgtgat     540
tatgacggtg gtcccacatt cgccacgcgc cagcagcaga tcgggttttg ccctaggaaa     600
cagcgtccag tgcagagacc tgtgtggcag agtggagagg agtactcttt tggtgagttc     660
gagtttaaag cgaagaactt tgagaagaat tatctcaaga aatgtggtaa aaagagtcaa     720
ctctctgccc ttgaaattga aacactttac tggagagcca ctgtggataa acccttctct     780
gttgagtatg ccaatgacat gcctggctcg gcttttatcc ctctgagtct ggctgctgcg     840
aggaggagag agtctggtgg tgaaggagga acagttggtg agaccgcttg gaacatgagg     900
gcaatgtcta gagccgaagg atcattgctt aagttcatga aggaagagat ccctggagtt     960
acatcaccaa tggtgtatgt tgctatgatg tttagttggt ttgcttggca tgtggaggac    1020
catgaccttc atagtctcaa ttacttgcat atgggtgctg gtaagacttg gtacggtgtg    1080
ccaaaggatg ctgctctggc ttttgaggag gttgttaggg ttcatggtta cggtgaagag    1140
ctcaatcctc ttgtgacatt ttctactctt ggtgagaaga caactgtgat gtctcctgaa    1200
gtatttgtta aagccggaat accgtgttgc aggttagtgc aaaatcctgg agagtttgtc    1260
gtcacctttc cgggagctta tcattcggga tttagtcatg gatttaattt tggagaagca    1320
tctaacattg ccactcccga atggttgaga atggctaaag atgctgctat ccggcgagct    1380
gctataaatt accctccaat ggtttctcat ctccagctac tttatgactt tgtattggct    1440
ctaggttcta gagtgccaac aagcatcaat cccaaaccac ggagttctag attaaaagat    1500
aaggcaagaa gcgaaggaga aagattgacc aaaaagctat tgtgcaaaa cattatccac     1560
aacaacgaat tgctttcttc tctcggaaaa ggatccccag tggcccttct cccacagagt    1620
tcctcagata tatcagtttg ttctgacctg cgaattggat cccatttgat aaccaaccag    1680
gaaaacccaa tccagttaaa gtgtgaggac ttaagttctg atagtgttgt ggttgatctc    1740
agtaacggtt taaaggatac agtttcagtg aaagaaaaat ttacatcttt atgtgaaagg    1800
agcagaaatc acctagcaag cacggagaag gacactcaag aaactctgtc tgatgctgaa    1860
aggaggaaga atgatgcagc tgttgcgctt tcggatcaaa ggcttttctc ttgtgttaca    1920
tgtggagtct taagctttga ttgtgtagct atcgttcaac ctaaagaagc agctgctaga    1980
tatctcatgt ctgcagattg tagcttcttc aatgattgga cagctgcttc tggatctgca    2040
aatcttggtc aggctgcaag atcacttcat cctcaaagca aagagaagca tgatgtaaat    2100
tacttctaca tgttcctgt tcaaactatg gatcattcag tgaagactgg cgatcaaaaa    2160
acttcaacaa cttcccccgac aatagcgcat aaagataatg atgttcttgg gatgttagct    2220
tcagcatatg gagactcttc tgattccgag gaagaagatc aaaaaggctt agttacccct    2280
```

-continued

```
agttccaaag gggaaacaaa aacgtatgat caagaaggtt cagatggcca tgaggaggct      2340
agagatggta gaacttctga ttttaactgc cagagactaa ccagcgaaca gaatgggtta      2400
agcaaaggcg gaaaatcatc acttctggaa atagctttac catttattcc aagatctgat      2460
gacgattcat gtcggttgca cgtgttttgt cttgagcatg ctgcgaagt ggaacagcaa       2520 cttcgtcctt ttgggggat taacttaatg ttactgtgcc atccagagta ccccaggata       2580
gaggctgaag caaagatagt tgccgaagag ctcgtcatca atcacgaatg gaatgatact      2640
gaattcagga atgtgacccg agaggatgag gaaacgattc aggcagcgtt ggataatgtt      2700
gaagctaagg gtgggaacag tgattggacc gtaaaattgg gtgttaacct tcttacagc       2760 gctattctca gtcgctctcc tctgtacagt aagcagatgc cgtataactc catcatatac      2820
aaggcgttcg gtcgcagctc tccagtagcg agctcaccct cgaaacccaa agtctctggt     2880 aaagatcgt ccagacagag gaaatatgtt gttggaaaat ggtgtggtaa ggtttggatg      2940
tcacatcagg tgcatccctt tttgctggag caggacttag aggggaaga atctgaaaga     3000 agttgtcatc ttcgagttgc tatggatgag gatgccactg gaaagagatc gtttcctaat      3060
aatgttccca gggattcgac aacaatgttt ggaagaaagt attgtaggaa gagaaagata     3120
agagcaaagg cggtgccacg caagaagctt acttctttta gagggaaga tggagtttct     3180 gatgacacat cagaagatca ttcttataag cagcaatgga gggcttccgg gaatgaggaa     3240
gagtcttatt ttgagacagg gaacacagct tctggtgatt catcaaatca aatgtctgat     3300
ccgcacaagg gaattatcag acataaaggt tataaagaat ttgagtcaga tgatgaggtt     3360
tcagaccgtt cacttgggga agagtatact gtacgggcat gtgcagcttc agagagctca     3420
atggagaatg gctctcagca ttcaatgtat gaccatgatg atgatgatga tgatatcgac      3480
aggcagccta gggggattcc aaggagccaa cagacaagag ttttttaggaa tccagtttca     3540 tatgagtcag aagataatgg cgtttatcag caaagcggaa gaatatccat aagtaatagg     3600
caagctaatc gaatggttgg tgaatatgat tcagcagaga attctttgga ggaacgaggc    3660
ttttgcagta cagggaaaag gcaaaccagg tcaacagcca aacgaatagc aaaaaccaag    3720
acagttcaga gttcgagaga cacaaaaggt cgcttttttgc aagaatttgc atctggaaag   3780
aagaatgaag aattggattc atacatggag ggacctagca cacggcttag ggtgagacat    3840
cagaagccgt cgagagggtc tttagaaaca aaaccaaaga agattggtaa gaagagaagt    3900
ggtaatgctt ccttctccag agttgcaact gaaaaagatg tggaggaaaa agaagaagaa    3960
gaagaagaag agaatgagga gagggaatgt gcagcatacc aatgtaacat ggagggttgc   4020
acgatgagtt tcagttcgga aaaacagttg atgttacaca aaagaaacat atgcccaatt    4080
aaaggctgtg gtaaaaactt cttctcacac aagtatttgg ttcaacacca gcgtgttcac    4140
tcagacgacc gtcctctgaa atgtccatgg aagggatgta agatgacgtt caagtgggct    4200
tggtctagaa ccgagcacat aagggttcac acaggcgcta ggccttatgt ttgcgctgaa    4260
ccggattgtg gtcaaacatt caggtttgtc tctgacttca gccggcataa aaggaagacc   4320
ggtcattcgg ttaagaagac caacaaaagg tgatttaggc tctaacatgg aatctatcat    4380
gaagaagatt actccattga tctattagaa gaaaattgga ttgtacgaat attagggggtt   4440 ttctaagtgt gtatgtctct ctggtcctct gtcaattcgg gattataaag tcaaagtctt    4500
aacatttgga atagccattg tttgttgcag acgtttttcac tttcagacag attctctctt   4560
tgttgtattc tctat                                                     4575
```

<210> SEQ ID NO 23
<211> LENGTH: 5841
<212> TYPE: DNA
<213> ORGANISM: Arabidopsis thaliana
<220> FEATURE:
<221> NAME/KEY: variation
<222> LOCATION: (1)...(5841)
<223> OTHER INFORMATION: ein6 mutant gene

<400> SEQUENCE: 23

```
gtgcaaacgg atttacagag aggacaacaa caaatgtgtg ttagaaatgg cagaatcgta      60
aataataaga aaatcatacc cttttaaaaa ccatttctct ctctaactaa gtgttcttta     120
cttgttttaa tacagagata tcacaatctc ttgctctgcc caaacccatc ccaaccccct     180
aaaaaaaata caattttttc ctctgtttct ttaatccaat aaaaacagag agacctaaga     240
aacgagatca acaaagcccg tcgtttttt cgaggaaaag tgaatgaccc tttaagaaaa      300
taactctatt ggccggagaa atggtggaga ctcgtcgatt ctcttaaagt ttgtttttt      360
ttcctctctt caaaattttt gttctgttta tactctgtaa tggcgtttta atttgatacc     420
tagaagttaa agtgaacaaa ttttgagaga agtctctttt ttttgttct tccctgtgtg      480
tgtgagagag agagagagat atggcggttt cagagcagag tcaagatgtg tttccatggc     540
ttaaatcgtt accggttgct ccagagttca gacctactct agcagagttt caagatccga     600
tcgcttacat tttgaagatt gaagaagaag cttctagata tggaatctgt aaaattctgc     660
ctccactgcc tcctccttcc aaaaaaacct cgatttctaa tctcaaccgt tctctggcgg     720
caagagcggc ggcgagggtt cgtgacggcg gctttggcgc gtgtgattat gacggtggtc     780
ccacattcgc cacgcgccag cagcagatcg ggttttgccc taggaaacag cgtccagtgc     840
agagacctgt gtggcagagt ggagaggagt actcttttgg tgagttcgag tttaaagcta     900
agaactttga gaagaattat ctcaagaaat gtggtaaaaa gagtcaactc tctgcccttg     960
aaattgaaac actttactgg agagccactg tggataaacc cttctctgtt gagtatgcca    1020
atgacatgcc tggctcggct tttatccctc tgagtctggc tgctgcgagg aggagagagt    1080
ctggtggtga aggaggaaca gttggtgaga ccgcttggaa catgagggca atgtctagag    1140
ccgaaggatc attgcttaag ttcatgaagg aagagatccc tggagttaca tcaccaatgg    1200
tgtatgttgc tatgatgttt agttggtttg cttggcatgt ggaggaccat gaccttcata    1260
gtctcaatta cttgcatatg ggtgctggta agacttggta cggtgtgcca aaggatgctg    1320
ctctggcttt tgaggaggtt gttagggttc atggttacgg tgaagagctc aatcctcttg    1380
gtgagtatga taagtgttat gtgttagtga ctcatagtta ctcaatgtat caattcattg    1440
ttctgattgt tggctttgtt gtgtctctgt tcttttttgtt gcttttaaat gcttttctttt  1500
ccctccaaaa gttgtcaggg gtagaagctg tatgcaagca aactaattgg ttatgcctct    1560
tacgttcttg tcttattagt gacatttttct actcttggtg agaagacaac tgtgatgtct   1620
cctgaagtat ttgttaaagc cggaataccg tgttgcaggt aatggttttt tatgtttgtg    1680
ctctgtttat ctcatcatct tgttgtttgc atgtctcttc tttggtctct tataattggc    1740
acacttttc ttcttctggt ttttcacgca agtggttttt ttgtatcagg ttagtgcaaa     1800
atcctggaga gtttgtcgtc accttttccgg gagcttatca ttcgggattt agtcatggtg   1860
agtaagcgac ctatattag tatctttaag tcaaccattc aaaggcctag tatgttgaaa     1920
taacttatat tatccataaa acaatcgtg ggggttgtac aggatttaat tttgagaag      1980
catctaacat tgccactccc gaatggttga gaatggctaa agatgctgct atccggcgag    2040
```

-continued

```
ctgctataaa ttaccctcca atggtttctc atctccagct actttatgac tttgtattgg    2100
ctctaggttc taggtactct ttcttttcta tagacacact caaactttt aagctgcttg      2160 aagggctcat ataaggtatg tttcactcat tgcagagtgc caacaagcat caatcccaaa    2220
ccacggagtt ctagattaaa agataaggca agaagcgaag gagaaagatt gaccaaaaag    2280
ctatttgtgc aaaacattat ccacaacaac gaattgcttt cttctctcgg aaaaggatcc    2340
ccagtggccc acagagttcc tcagatatat cagtttgttc tgacctgcga attggatccc    2400
atttgataac caaccaggaa aacccaatcc agttaaagtg tgaggactta agttctgata    2460
gtgttgtggt tgatctcagt aacggtttaa aggatacagt ttcagtgaaa gaaaaattta    2520
catctttatg tgaaaggagc agaaatcacc tagcaagcac ggagaaggac actcaagaaa    2580
ctctgtctga tgctgaaagg aggaagaatg atgcagctgt tgcgctttcg gatcaaaggc    2640
ttttctcttg tgttacatgt ggagtcttaa gctttgattg tgtagctatc gttcaaccta    2700
aagaagcagc tgctagatat ctcatgtctg cagattgtag cttcttcaat gattggacag    2760
ctgcttctgg atctgcaaat cttggtcagg ctgcaagatc acttcatcct cgtaagttac    2820
aggtcgcact ttcggttatt ggctgttatt tagcatttac taactttttt tcatcatgca    2880
gaaagcaaag agaagcatga tgtaaattac ttctacaatg ttcctgttca aactatggat    2940
cattcagtga agactggcga tcaaaaaact tcaacaactt ccccgacaat agcgcataaa    3000
gataatgatg ttcttgggat gttagcttca gcatatggag actcttctga ttccaggaa    3060 gaagatcaaa aaggcttagt taccoctagt tccaaagggg aaacaaaaac gtatgatcaa    3120
gaaggttcag atggccatga ggaggctaga gatggtagaa cttctgattt taactgccag    3180
agactaacca gcgaacagaa tgggttaagc aaaggcggaa atcatcact tctggaaata    3240 gctttaccat ttattccaag atctgatgac gattcatgtc ggttgcacgt gttttgtctt    3300
gagcatgctg cggaagtgga acagcaactt cgtccttttg gggggattaa cttaatgtta    3360
ctgtgccatc caggtaacat caaaactaca agattcattt tattagtatt tctgtatcag    3420
ttatgcaatt ctttagtctt tttcatcatt ttgacgcaca acatttgcag agtaccccag    3480
gatagaggct gaagcaaaga tagttgccga agagctcgtc atcaatcacg aatggaatga    3540
tactgaattc aggaatgtga cccgagagga tgaggaaacg attcaggcag cgttggataa    3600
tgttgaagct aagggtggga acagtgattg gaccgtaaaa ttgggtgtta acctttctta    3660
cagcgctatt ctcagtcgct ctcctctgta cagtaagcag atgccgtata actccatcat    3720
atacaaggcg ttcggtcgca gctctccagt agcgagctca ccctcgaaac ccaaagtctc    3780
tggtaaaaga tcgtccagac agaggaaata tgttgttgga aaatggtgtg gtaaggtttg    3840
gatgtcacat caggtactat tgtctaacct gaatccatac taattcagac attagtacac    3900
ttctgttggg ttcaatttgc ttttctttct tcaggtgcat ccctttttgc tggagcagga    3960
cttagagggg aagaatctg aaagaagttg tcatcttcga gttgctatgg atgaggatgc    4020
cactggaaag agatcgtttc ctaataatgt ttccagggat tcgacaacaa tgtttggaag    4080
aaagtattgt aggaagagaa agataagagc aaaggcggtg ccacgcaaga agcttacttc    4140
ttttaagagg gaagatggag tttctgatga cacatcagaa gatcattctt ataagcagca    4200
atggagggct tccggaatg aggaagagtc ttattttgag acagggaaca cagcttctgg    4260
tgattcatca aatcaaatgt ctgatccgca caagggaatt atcagacata aaggttataa    4320
agaatttgag tcagatgatg aggtttcaga ccgttcactt ggggaagagt atactgtacg    4380
ggcatgtgca gcttcagaga gctcaatgga gaatggctct cagcattcaa tgtatgacca    4440
```

```
tgatgatgat gatgatgata tcgacaggca gcctaggggg attccaagga gccaacagac    4500
aagagttttt aggaatccag tttcatatga gtcagaagat aatggcgttt atcagcaaag    4560
cggaagaata tccataagta ataggcaagc taatcgaatg gttggtgaat atgattcagc    4620
agagaattct ttggaggaac gaggcttttg cagtacaggg aaaaggcaaa ccaggtcaac    4680
agccaaacga atagcaaaaa ccaagacagt tcagagttcg agagacacaa aaggtcgctt    4740
tttgcaagaa tttgcatctg gaaagaagaa tgaagaattg gattcataca tggagggacc    4800
tagcacacgg cttagggtga gacatcagaa gccgtcgaga gggtctttag aaacaaaacc    4860
aaagaagatt ggtaagaaga gaagtggtaa tgcttccttc tccagagttg caactgaaaa    4920
agatgtggag gaaaaagaag aagaagaaga agaagaagag aatgaggaag aggaatgtgc    4980
agcataccaa tgtaacatgg agggttgcac gatgagtttc agttcggaaa aacagttgat    5040
gttacacaaa agaaacatat gcccaattaa aggctgtggt aaaaacttct tctcacacaa    5100
gtatttggtt caacaccagc gtgttcactc agacgaccgt cctctgaaat gtccatggaa    5160
gggatgtaag atgacgttca agtgggcttg gtctagaacc gagcacataa gggttcacac    5220
aggcgctagg ccttatgttt gcgctgaacc ggattgtggt caaacattca ggtttgtctc    5280
tgacttcagc cggcataaaa ggaagaccgg tcattcggtt aagaagacca acaaaaggtg    5340
atttaggctc taacatggaa tctatcatga agaagattac tccattgatc tattagaaga    5400
aaattggatt gtacgaatat tagggttttt ctaagtgtgt atgtctctct ggtcctctgt    5460
caattcggga ttataaagtc aaagtcttaa catttggaat agccattgtt tgttgcagac    5520
gttttcactt tcagacagat tctctctttg ttgtattctc tattttttgca gttgaatgaa    5580 tctgtaacaa caacaaatcc tggtgtagga aaagcattgt gttactcaag tatttgacat    5640
atatggttgt atacgtggct tatcctggtt ggttgacagt cagagttcat cgccgtggac    5700
ttcatttgac tttgataaag actcaaacct accaaattgc taatgaatga cattacctgt    5760
gtcaactagg atgtaaaact ctctgacttc agcacacggc acaaacgaaa gaccaaatga    5820
cttaacattt ggaattgcca t                                              5841
```

ETHYLENE INSENSITIVE PLANTS

RELATED APPLICATIONS

This application is a divisional application of U.S. Ser. No. 10/144,156, filed on May 10, 2002 now abandoned, which claims priority from U.S. Provisional Application No. 60/290,303 filed on May 10, 2001, which is incorporated here in by reference in its entirety.

GOVERNMENTAL SUPPORT

This work was supported in part by research grants from the National Science Foundation MCB0049003 and Department of Energy grant ER15113. The U.S. government may have certain rights to this invention.

BACKGROUND OF THE INVENTION

1. Field of the Invention

The field of the invention relates to plants and plant genes, including both plant mutants and transgenic plants containing a gene that confers an ethylene insensitive phenotype. Also encompassed by the invention are methods of using the disclosed plant gene to confer an ethylene insensitive phenotype.

2. Description of the Related Art

The plant hormone ethylene plays a central role in a variety of processes, including wounding, pathogen attack, cell fate and elongation, senescence, and fruit ripening. The classical triple response to ethylene, inhibited hypocotyl and root elongation, thickening of the hypocotyl, and exaggeration of the apical hook, has been used to study the signaling pathway that mediates this hormone response. Molecular genetic studies in *Arabidopsis thaliana* have exploited the triple response to ethylene, and resulted in the identification of mutants defective in this response. Epistasis studies with plants that are insensitive to the hormone or display a constitutive response to ethylene have suggested a signaling pathway in which one group of proteins acts to antagonize pathway activity in the absence of the hormone, and a second group functions to transmit the signal and initiate physiological responses.

The ETR1 gene and a family of related genes, including EIN4, ETR2, ERS1, and ERS2, encode ethylene receptors. Ethylene binding is mediated by the hydrophobic amino terminus of ETR1 in a copper dependent manner. Point mutations in this domain can disrupt ethylene binding, and result in dominant ethylene insensitivity, suggesting that the proteins actively suppress pathway activity in the absence of the hormone, and that ethylene binding removes this inhibitory activity. Genetic experiments in which combining loss of function alleles of at least three family members resulted in constitutive pathway activity in the absence of ethylene confirmed the idea that the receptors negatively regulate ethylene signaling in the absence of the hormone. The important role copper plays in receptor function was underscored by the identification of the RAN1 gene, which bears significant sequence similarity to the Menkes/Wilson disease copper transporter. Disruption of RAN1 by mutation or co-suppression resulted in plants that display a constitutive triple response, suggesting that copper is required for the nominal formation or proper structure of a receptor complex in addition to ethylene binding.

Mutation of the Raf kinase homolog CTR1 also results in a constitutive triple response in the absence of ethylene. Based on epistasis studies, CTR1 functions downstream of the ethylene receptors, and represses signaling pathway activity in the absence of the hormone. The repressive roles played by both CTR1 and the receptors suggests a functional link between the two. Indeed, protein interaction studies have shown that CTR1 and ETR1 physically interact, but the manner by which ETR1 may activate CTR1 is unknown. Although the homology of CTR1 to Raf suggests a downstream MAP kinase signaling cascade, the manner by which CTR1 represses ethylene signaling is also unknown.

Mutations of the EIN2 gene are recessive and also confer complete ethylene insensitivity. Epistasis testing indicates that EIN2 functions downstream of CTR1, and consequently is thought to play a central role in ethylene responses. EIN2 possesses an amino terminus that is predicted to contain multiple transmembrane domains, and is similar to metal transporters of the Nramp family. The exact manner in which EIN2 functions to activate the ethylene signaling pathway is unclear, however it has been shown that expression of its carboxyl end is sufficient to stimulate ethylene-dependent effects, including the triple response.

Terminal components of the primary ethylene signaling pathway are encoded by the EIN3 gene and a related family of EIL genes. ein3 mutations partially block activation by both ctr1 mutations and the EIN2 carboxyl end, indicating that it functions downstream of EIN2 in the signaling cascade. EIN3 and EIL proteins represent a novel class of transcription factors, and have been found to bind as dimers to a unique site found in some promoters of a second class of transcription factors termed ethylene response element binding proteins (EPEBP). Many of these factors bind to the GCC box found in many ethylene responsive genes that are activated several hours after ethylene treatment. An EIN3 binding site was found in the promoter of one such factor, ERF1, which was activated within fifteen minutes of ethylene treatment in an EIN3-dependent manner. Overexpression of ERF1 activated a subset of ethylene responses and bypassed an ein3 mutation, indicating that it functions downstream of EIN3 in the signaling cascade. These data indicate that a complete ethylene response is mediated by a series of transcription factors that act in sequential steps. EIN3 and EIL proteins act very early in the transcriptional cascade, whereas ERF1 and related proteins act later.

Roman et al. described a mutant plant, ein6 (Roman, et al. (1995) "Genetic analysis of ethylene signal transduction in *Arabidopsis thaliana:* five novel mutant loci integrated into a stress response pathway" Genetics 139(3): 1393–1409) This mutant plant demonstrated ethylene insensitivity, which was assumed to be the result of a single recessive mutation. The EIN6 gene was not identified. Unlike etr1 and ein2 mutants, ein6 mutant plants were found to retain some sensitivity to ethylene, with the root being less sensitive to ethylene than the hypocotyl. However, the original work mischaracterized the ein6 mutant plant as the phenotype was thought to be due to a single mutation.

In addition, the chromosomal location and DNA/Protein sequence of the EIN6 gene was not described, thus hindering in-depth studies of this mutation. However, as described below, the present application describes the isolation and characterization of the EIN6 gene, as well as the mutant allele, ein6.

SUMMARY OF THE INVENTION

One embodiment of the invention is a mutant plant containing a mutated form of the EIN6 gene, wherein said mutant plant exhibits an altered response to ethylene. In a preferred embodiment, the altered response to ethylene includes an ethylene insensitive or an ethylene insensitive root (EIR) phenotype. In a more preferred embodiment, the mutant plant contains an ein6 gene which has the nucleotide sequence shown in SEQ ID NO: 23.

Another embodiment of the invention is a mutant plant containing a mutated form of the EIN6 and a mutated form of the ein gene. This double mutant plant was found to be ethylene insensitive throughout the plant, in contrast to the EIR phenotype found in ein6 single mutants.

Another embodiment of the invention relates to the discovery that the ein6/een mutation was found to be epistatic to ctr1, partially suppressing the constitutive hormone response in a manner similar to ein3 mutations. In these respects, ein6/een double mutants were very similar to other ethylene insensitive mutants. Interestingly, certain phenotypes of the ein6/een double mutant distinguish it from other ethylene-related mutants, such as hypersensitivity to the microtubule-stabilizing drug taxol.

The present application describes the isolation and characterization of the EIN6 gene, which was found to be required for normal ethylene responses. The EIN6 gene encodes a protein containing multiple zinc fingers, and additional domains that are implicated in protein-protein interactions. As such, it represents an excellent candidate for a partner of EIN3 or ERF1 in the regulation of ethylene-dependent transcription.

Another embodiment of the invention is drawn to an isolated polynucleotide having a nucleic acid sequence that hybridizes to the sequence of SEQ ID NO: 22 under moderate stringency, wherein expression of the polynucleotide in a plant results in an altered response to ethylene. In a preferred embodiment, the isolated polynucleotide has the sequence shown in SEQ ID NO: 23. Also encompassed within the present invention is a plant expression vector containing an isolated polynucleotide that hybridizes to the sequence of SEQ ID NO: 22 under moderate stringency, operably linked to a promoter, wherein expression of the polynucleotide in a plant results in an altered response to ethylene. In one embodiment, the promoter is a constitutive promoter. In an alternate embodiment, the promoter is a tissue specific promoter. In another alternate embodiment, the promoter is an inducible promoter.

Also included within the invention is a method for producing a transgenic plant with an altered ethylene-dependent phenotype including the steps of:

transforming a plant cell with a plant expression vector containing the isolated polynucleotide that hybridizes to the sequence of SEQ ID NO: 22 under moderate stringency;

regenerating a transgenic plant from the transformed plant cell;

growing said transgenic plant under conditions such that the isolated polynucleotide is expressed in the plant; and selecting at least one plant having an altered ethylene-dependent phenotype.

In one embodiment, the altered ethylene-dependent phenotype is selected from the group including ripening, flowering, senescence, browning, and sensitivity to pathogens. In a more preferred embodiment, the plant expression vector contains the nucleotide sequence of SEQ ID NO: 22. In one preferred embodiment, the polynucleotide is overexpressed in the plant. In another preferred embodiment, expression of the polynucleotide inhibits expression of a corresponding gene. In a most preferred embodiment, the polynucleotide transcribes an RNA that is complementary to that gene.

Also encompassed within the invention is an isolated polypeptide containing the amino acid sequence of SEQ ID NOS: 20 or 21.

Also included in embodiments of the invention is an isolated polynucleotide encoding an EIN6 gene as well as polynucleotides which have 80%, 85%, 90%, or 95% homology to SEQ ID NO: 22.

In another embodiment, the invention includes a recombinant expression vector containing a polynucleotide sequence encoding an EIN6 gene. In a further embodiment, the present invention includes a bacterial or plant host cell containing the recombinant vector containing the EIN6 gene.

Another embodiment of the invention includes a genetically modified plant containing at least one exogenous nucleic acid sequence encoding an EIN6 gene. Also included are embodiments of the invention wherein the exogenous nucleic acid sequence has at least 80%, 85%, 90%, or 95% homology to the sequence of SEQ ID NO: 22. In a further embodiment the exogenous nucleic acid sequence of the genetically modified plant contains a regulatory nucleic acid sequence. In a preferred embodiment, the regulatory sequence is a promoter. In a more preferred embodiment, the promoter is a constitutive promoter. In an alternate more preferred embodiment, the promoter is an inducible promoter. In another alternate preferred embodiment, the promoter is a tissue specific promoter. In a preferred embodiment, the exogenous nucleic acid sequence in the genetically modified plant contains a selectable marker. In a preferred embodiment, the genetically modified plant is a dicotyledonous plant. In an alternate preferred embodiment, the genetically modified plant is a monocotyledonous plant. Also encompassed by the present invention are seeds which germinate into a plants containing at least one exogenous nucleic acid sequence encoding an EIN6 gene.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIGS. 2A and 2B: Nucleotide Sequence of the EIN6 Gene (SEQ ID NO: 1). The genomic sequence of the EIN6 gene from the Landsberg erecta ecotype was determined by direct sequencing of overlapping PCR products covering the locus. Nucleotides are numbered with the first nucleotide of the cDNA being +1. Exons are listed in capital letters, whereas introns are in lowercase. Asterisks above the line indicate the 7 nucleotides deleted in the ein6 mutant, and solid boxes above the nucleotides denote an intron that is removed by alternative splicing.

FIGS. 2A and 2B: Amino Acid Sequence of the EIN6 Polypeptides. This figure shows the amino acid sequence of the full length EIN6 protein (SEQ ID NO: 20). The solid box above the sequence denotes a putative coil domain. The vertically-hatched box above the sequence denotes a putative ATP/GTP-binding P-loop domain. The asterisks above the sequence denote putative nuclear localization signals. The diagonally-hatched boxes above the sequence indicate acidic domains.

FIG. 4. This figure shows the amino acid sequence of the alternatively-spliced EIN6 gene product (SEQ ID NO: 21).

FIG. 5. Alignment of Zinc Finger Motifs. The sequence of the EIN6 zinc finger domains (SEQ ID NO: 2) aligned with other zinc finger domain-containing proteins. GLI1 (SEQ ID NO: 3) and GLI3 (SEQ ID NO: 5) zinc finger proteins from *Mus musculus*. X84986 (SEQ ID NO: 4) is a putative zinc finger protein from *Drosophila melanogaster*. SPH1-BF (SEQ ID NO: 6) is the SPH1 binding factor from *Homo sapiens*. RPH1p (SEQ ID NO: 7) is the repressor of photolyase gene from *Saccharomyces cerevisiae*. Identical residues are highlighted by black boxes, and similar residues are indicated by shading. Numbers indicate the positions of the residues within the respective polypeptides.

FIG. 6. Alignment of the EIN6 amino terminus with two interrupted domains of homology. The sequence of the EIN6 amino terminal domain (SEQ ID NO: 8) aligned with proteins whose homology extend over two non-contiguous regions. The EIN6 sequence is listed as contiguous, but only the homologous regions of related proteins are shown. The regions of homology are interrupted by a 300 amino acid domain in the homologous proteins. RBP2 is the retinoblastoma binding protein 2 of Homo sapiens (SEQ ID NO: 9). Smcx (SEQ ID NO: 10) is an X-linked protein not subject to X-linked inactivation from *Mus musculus*. CG9088 (SEQ ID NO: 11) is a predicted protein from *Drosophila melanogaster*. AL136078 (SEQ ID NO: 12) is a predicted protein from *Schizosaccharomtyces pombe*. F2K11.14 (SEQ ID NO: 13) is a predicted protein from *Arabidopsis thaliana*. Identical residues are highlighted by black boxes, and similar residues are indicated by shading. Numbers indicate the positions of the residues within the respective polypeptides.

FIG. 7. Alignment of the EIN6 Amino Terminus (SEQ ID NO: 14) with a Continuous Domain of Homology. The sequence of the EIN6 amino terminal domain aligned with proteins whose homology extend over a single continuous sequence. RPH1p (SEQ ID NO: 15) is the repressor of photolyase gene from *Saccharomyces cerevisiae*. F19I3.11 (SEQ ID NO: 16) is a predicted protein from *Arabidopsis thaliana*. CG4037 (SEQ ID NO: 17) is a predicted protein from *Drosophila melanogaster*. Y48B6A.11 (SEQ ID NO: 18) is a hypothetical protein from *Caenorhabditis elegans*. KIAA0780 (SEQ ID NO: 19) is a predicted protein from *Homo sapiens*. Identical residues are highlighted by black boxes, and similar residues are indicated by shading. Numbers indicate the positions of the residues within the respective polypeptides.

DETAILED DESCRIPTION

Figure 1:
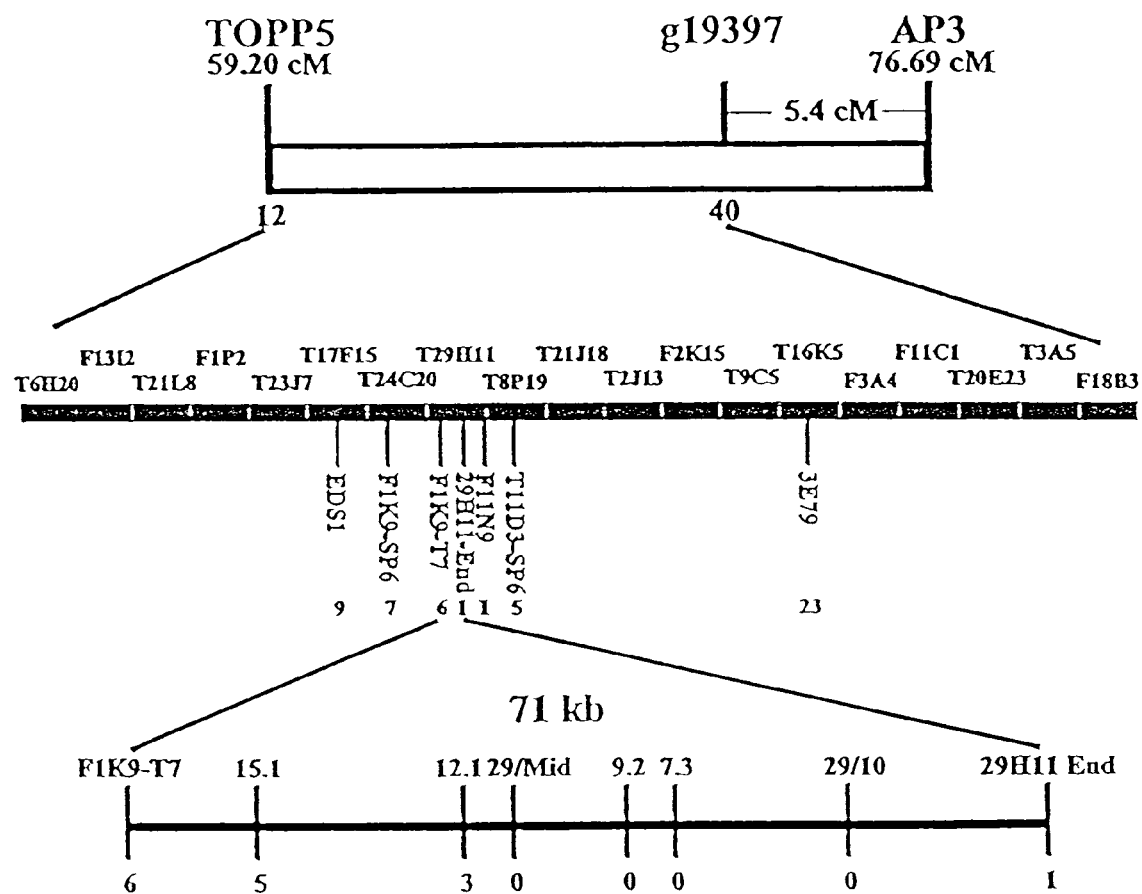
FIG. 1. Genetic and Physical Map of the EIN6 Genomic Region. Genomic region shown corresponds to the middle of chromosome 3, "proximal" and "distal" referring to the orientation relative to the centromere. The CAPS markers TOPP5 and g19397 were mapped relative to the EIN6 gene, and map positions of TOPP5 and AP3, and genetic distance between the g19397 and AP3 markers are based on published recombinant inbred mapping data. The numbers below TOPP5 and g19397 the chromosomal map reflect the number of recombinant plants identified out of populations of 124 and 350 F2 plants, respectively. The BAC contig for this interval is the ESSA sequencing contig for this region of chromosome 3. The numbers below the markers for this map represent the number of recombinant plants identified out of a population of 496 F2 plants. The marker locations of the 71 kb interval of T29H11 were determined from the genomic sequence determined by the ESSA Sequencing Consortium. The numbers below the markers are the number of recombinant plants identified out of a population of 496 F2 plants.

Embodiments of the invention are based, in part, upon the identification, isolation, cloning and sequencing of a novel gene family regulating developmental and stress responses in plants, including the classical triple response to ethylene. Described below are genomic (SEQ ID NO: 1) and cDNA (SEQ ID NO: 22) sequences of the EIN6 gene, homologues, mutants, and fragments thereof. In addition, a specific mutated sequence of ein6 with a 7 base pair deletion is specifically described (SEQ ID NO: 23). Also disclosed is a sequence for the full length polypeptide, identified in *Arabidopsis thaliana* (SEQ ID NO: 20). A second protein, produced by alternate splicing, is also described (SEQ ID NO: 21).

A mutation in the novel ethylene-signaling gene Ethylene Insensitive 6 (EIN 6) was identified from a large pool of fast neutron mutagenesis-treated *Arabidopsis* (Landsberg ecotype) seed (Example 1). The mutagenized pool was screened for lines that were insensitive to ethylene (Roman et al., 1995). Ethylene insensitive mutants found by this screening method did not display the characteristic seedling triple response to the hormone. In addition to ein6, the screen also identified a number of other ethylene pathway mutants such as ein4, ein5, ein7 and eir1. The ein6 mutant had a moderately ethylene insensitive phenotype, weaker than that of the strong ethylene insensitive mutant ein2.

The ein6 mutation was found to be a recessive mutation that was classified by having significantly reduced gametophytic transmission. The reduced transmission was originally attributed to the existence of possible chromosomal aberrations caused by the fast neutron-mutagenesis. The gene was originally mapped to the bottom of chromosome 3, between the markers GL1, and nga112. It was hypothesized to be a reduction of function mutant, rather than a loss of function mutant, because of its moderate ethylene insensitive phenotype. The nucleic acid sequence of the 7 bp deletion in the ein6 mutation was identified using denaturing high performance liquid chromatography as described in Example 2.

Further genetic analysis showed that the original ein6 mutant line described by Roman et al. was actually a double mutant (see Example 3) containing a mutation in both the EIN6 gene, plus an enhancer mutation currently being called ENHANCER OF ETHYLENE INSENSITIVITY (EEN) (see Example 6). The finding of the presence of the double mutation explains the earlier finding of the reduced transmission phenotype mentioned above. Thus, the screening assays revealed a series of ein6/een double mutant plants. Unlike strong insensitive mutants, such as etr1 and ein2, the ein6/een double mutants were found to still retain some ethylene sensitivity.

The analysis of ethylene response pathway double mutants is a useful method to elucidate EIN6 function and its relation to other ethylene pathway members. Epistasis relationships between mutations in a biochemical or regulatory pathway can provide information about the way these genes interact without any a priori knowledge of their molecular identity (Ferguson et al. 1987; Chory 1990). To define the relationship between ethylene mutants, double mutants were isolated as described in Example 12. The triple-response phenotypes of wild-type, single and double mutant strains were quantified in the presence and absence of ethylene.

The EIN6 gene was found to encode a protein of 1359 amino acids, having three zinc fingers and three putative nuclear localization sites (see Example 5). Embodiments of the invention provide isolated nucleic acids including nucleotide sequences comprising or derived from the EIN6 genes and/or encoding polypeptides comprising or derived from the EIN6 proteins. EIN6 sequences include the specifically disclosed sequences, and splice variants, allelic variants, synonymous sequences, and homologous or orthologous variants thereof. Thus, for example, embodiments of the invention include genomic and cDNA sequences from the EIN6 gene.

Embodiments of the invention also include allelic variants and homologous or orthologous sequences. For example, these variants are useful in allele specific hybridization screening or PCR amplification techniques. Moreover, subsets of the EIN6 sequences, including both sense and antisense sequences, and both normal and mutant sequences, as well as intronic, exonic and untranslated sequences, may be employed for these techniques. Such sequences may comprise a small number of consecutive nucleotides from the sequences which are disclosed or otherwise enabled herein but preferably include at least 8–10, and more preferably 9–25, consecutive nucleotides from an EIN6 sequence. Various nucleic acid constructs in which EIN6 sequences, either complete or subsets, are operably joined to exogenous sequences to form cloning vectors, expression vectors, fusion vectors, transgenic constructs, and the like are also contemplated.

The location of EIN6 in the ethylene pathway has been difficult to determine because the original mutation was generated in the Ler ecotype and a majority of the other ethylene mutants are in the Col-0 ecotype. It has been determined that EIN6 is downstream of CTR1, based on a cross of ein6 to a Ler allele of ctr1. Sequence analysis of the putative polypeptide sequence encoded by the EIN6 gene has three nuclear localization signals, indicating that the EIN6 protein may be localized in the nucleus.

Interestingly, plants having only the ein6 mutant displayed an even greater selective insensitivity to ethylene, with the root being the only part of the plant that is fully insensitive. In contrast, plants having both the ein6 and the een mutation had an insensitivity to ethylene that is distributed throughout the entire plant rather than just in the root. Further characterization of the double mutant determined that seedlings possessing the ein6/een mutations were also hypersensitive to the microtubule-stabilizing drug taxol. This phenotype differentiated it from other ein mutants, and indicated that the EIN6 gene product played a role in phenomena that were unrelated to ethylene.

Accordingly, embodiments of the invention include the EIN6 gene and mutations thereof, as well as a characterization of the ein6/een double mutants which have been discovered in *Arabidopsis*. However, the disclosed methods are not limited to any particular plant type. It is expected that similar mutations in other plants will result in similar phenotypes.

In other embodiments of the invention, genetically modified plants having decreased levels of the functional EIN6 polypeptide, and further exhibiting decreased root sensitivity to ethylene, are provided.

In another embodiment of the invention, genetically modified plants having decreased levels of both EIN6 and EEN are provided. Such loss of function double mutant plants were found to have decreased sensitivity to ethylene throughout the entire plant. In addition, it was discovered that these double mutants had increased sensitivity to the drug taxol.

Nucleic Acids

The polynucleotides encoding EIN6 include the nucleotide sequences of SEQ ID NOS: 1, 22, and 23. A genomic sequence for EIN6 is shown in SEQ ID NO: 1. The corresponding cDNA sequence is shown in SEQ ID NO: 22 and one example of a mutant form of the ein6 gene is shown in SEQ ID NO: 23. Nucleic acid sequences complementary to SEQ ID NOS: 1, 22, and 23 are also encompassed within the present invention.

As used herein, the terms "polynucleotides" and "nucleic acid sequences" refer to DNA, RNA and cDNA sequences. A complementary sequence may include an antisense nucleotide. When the sequence is RNA, the deoxyribonucleotides A, G, C, and T of SEQ ID NOS: 1, 22, or 23 are replaced by ribonucleotides A, G, C, and U, respectively. Also included in the invention are fragments ("probes") of the above-described nucleic acid sequences that are at least 15 bases in length, which is sufficient to permit the probe to selectively hybridize to DNA that encodes the protein of either of SEQ ID NOS: 20 or 21.

Embodiments of the invention also provide an isolated polynucleotide sequence encoding a polypeptide having the amino acid sequence of either of SEQ ID NOS: 20 or 21. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode EIN6. It is understood that polynucleotides encoding all or varying portions of EIN6 are included herein, as long as they encode a polypeptide with EIN6 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription. Without being bound by any theory, SEQ ID NO: 21 is believed to represent a splice variant of SEQ ID NO: 20.

Moreover, EIN6 polynucleotides include polynucleotides having alterations in the nucleic acid sequence which still encode a polypeptide having the ability to modify the response to ethylene. Alterations in EIN6 nucleic acid include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences. A specific alteration of EIN6 comprising a 7 base pair deletion that results in a decreased response to ethylene, is exemplified herein (SEQ ID NO: 23).

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a template sequence in a mixture of genomic DNA without cloning or purification. This process for amplifying the template sequence consists of introducing a large excess of two oligonucleotide primers to the DNA mixture containing the desired template sequence, followed by a precise sequence of thermal cycling in the presence of a DNA polymerase. The two primers are complementary to their respective strands of the double stranded template sequence. To effect amplification, the mixture is denatured and the primers then annealed to their complementary sequences within the template molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired template sequence. The length of the amplified segment of the desired template sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the template sequence become the predominant sequences (in terms of concentration) in the mixture, they are said to be "PCR amplified".

With PCR, it is possible to amplify a single copy of a specific template sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Antisense" nucleic acids are DNA or RNA molecules that are complementary to at least a portion of a specific mRNA molecule (Weintraub (1990) Scientific American 262: 40). In the cell, the antisense nucleic acids hybridize to the corresponding mRNA, forming a double-stranded molecule. This interferes with the translation of the mRNA since the cell will not translate a mRNA that is double-stranded. Antisense oligomers of about 15 nucleotides are preferred, since they are easily synthesized and are less likely to cause non-specific interference with translation than larger molecules. The use of antisense methods to inhibit the in vitro translation of genes is well known in the art (Marcus-Sakura (1988) Anal. Biochem. 172: 289). In the present case, plants transformed with constructs containing antisense fragments of the EIN6 gene would display phenotypes such as prolonged shelf due to delayed ripening, delayed abscission, delayed senescence, and reduced browning.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under medium stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

"Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated EIN6 nucleotide sequences.

Also included in embodiments of the invention are nucleotide sequences that are greater than 70% homologous with any of the sequences shown in SEQ ID NOS: 1, 22, or 23, but still retain the ability to confer an ethylene-dependent phenotype. Other embodiments of the invention include nucleotide sequences that are greater than 75%, 80%, 85%, 90% or 95% homologous with any of the sequences shown in SEQ ID NOS: 1, 22, or 23, but still retain the ability to confer an ethylene-dependent phenotype.

Specifically disclosed herein are genomic and cDNA sequences for EIN6. DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of the EIN6 sequence encoding the protein in question, can be synthesized chemically. This requires that short, oligopeptide stretches of the amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981). Alternatively, a subtractive library is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., Nucl. Acid Res., 11:2325, 1983).

Expression studies of EIN6 can be performed using gene chip technologies. Although EIN6 appears to be a component of the ethylene signaling pathway, expression analysis of EIN6 (utilizing an Affymetrix GeneChip and other methods) has shown that EIN6 is not regulated by ethylene. The expression of the gene is moderate and can be easily seen in all conditions analyzed. In experiments using Columbia ecotype *Arabidopsis* plants grown in air and grown in exogenous ethylene, there is no difference in the expression of EIN6. There is also no dramatic difference in expression level of this gene in many of the ethylene mutants, such as ein5, ein2, hls, and cir1.

Embodiments of the invention also include functional EIN6 polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of EIN6 polypeptide", refers to all fragments of EIN6 that retain EIN6 activity, e.g., responsiveness to ethylene. Biologically functional fragments, for example, can vary in size from a polypeptide fragment as small as an epitope capable of binding an antibody molecule to a large polypeptide capable of participating in the characteristic induction or programming of phenotypic changes within a cell.

The polynucleotides described herein include sequences that are degenerate as a result of the genetic code. There are 20 natural amino acids, most of which are specified by more than one codon. Therefore, all degenerate nucleotide sequences are included in the invention as long as the amino acid sequence of EIN6 polypeptide encoded by such nucleotide sequences retains EIN6 activity. A "functional polynucleotide" denotes a polynucleotide which encodes a functional polypeptide as described herein. In addition, embodiments of the invention also include a polynucleotide encoding a polypeptide having the biological activity of an amino acid sequence of either of SEQ ID NOS: 20 or 21 and having at least one epitope for an antibody immunoreactive with EIN6 polypeptide.

EIN6 Polypeptides

Many modifications of the EIN6 primary amino acid sequence may result in plants having reduced or abolished ethylene responses. Such modifications may be deliberate, as by site-directed mutagenesis, or may be spontaneous. All of the polypeptides produced by these modifications are included herein as long as the biological activity of EIN6 is present. Further, deletion of one or more amino acids can also result in a modification of the structure of the resultant molecule without significantly altering its activity. This can lead to the development of a smaller active molecule which could have broader utility. For example, it may be possible to remove amino or carboxy terminal amino acids required for EIN6 activity.

EIN6 polypeptides include amino acid sequences substantially the same as the sequence set forth in SEQ ID NOS: 20 or 21, including mutants that result in plants having altered ethylene responsiveness. The term "substantially the same" refers to amino acid sequences that provide nearly the same amino acid sequence, or retain the activity of EIN6 as described herein. The EIN6 polypeptides of the invention include conservative variations of the polypeptide sequence.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Another aspect of the invention is polypeptides or fragments thereof which have at least about 70%, at least about 80%, at least about 85%, at least about 90%, at least about 95%, or more than about 95% homology to one of the polypeptides of SEQ ID NOS: 20 or 21, and sequences substantially identical thereto, or a fragment comprising at least 5, 10, 15, 20, 25, 30, 35, 40, 50, 75, 100, or 150 consecutive amino acids thereof. Homology may be determined using any of the methods described herein which align the polypeptides or fragments being compared and determines the extent of amino acid identity or similarity between them. It will be appreciated that amino acid "homology" includes conservative amino acid substitutions such as those described above.

Homologous amino acid or nucleotide sequences of the present invention preferably comprise enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool) (for a review see Altschul, et al., *Meth Enzymol.* 266:460, 1996; and Altschul, et al., *Nature Genet.* 6:119, 1994). BLAST is the heuristic search algorithm employed by the programs blastp, blastn, blastx, tblastn, and tblastx using the statistical methods of Karlin and Altschul (available at the NCBI website, Altschul, et al., *J. Mol. Biol.* 215:403, 1990). The BLAST programs were tailored for sequence similarity searching, for example to identify homologues to a query sequence. The BLAST pages offer several different databases for searching. Some of these databases, such a *e coli*, dbEST and month, are subsets of the NCBI (National Center for Biotechnology Information) databases, while others, such as SwissProt, PDB and Kabat are compiled from outside sources. Protein BLAST allows one to input protein sequences and compare these against other protein sequences.

The five BLAST programs available at Internet website: www.ncbi.nlm.nih.gov perform the following tasks:

blastp—compares an amino acid query sequence against a protein sequence database.

blastn—compares a nucleotide query sequence against a nucleotide sequence database.

blastx—compares the six-frame conceptual translation products of a nucleotide query sequence (both strands) against a protein sequence database.

tblastn—compares a protein query sequence against a nucleotide sequence database dynamically translated in all six reading frames (both strands).

tblastx—compares the six-frame translations of a nucleotide query sequence against the six-frame translations of a nucleotide sequence database.

Other computer program methods to determine identity and similarity between the two sequences include but are not limited to the GCG program package (Devereux, et al., *Nucl. Acids Res.* 12:387, 1984) and FASTA (Atschul, et al., *J Molec. Biol.* 215:403, 1990). By "percentage identity" is meant % of identical amino acids between the two compared proteins. By "% similarity" is meant the percentage of similar amino acids between the two compared proteins.

The polypeptides or fragments having homology to one of the polypeptides of SEQ ID NOS: 20 or 21, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described herein.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOS: 20 or 21, and sequences substantially identical thereto, or a fragment comprising at least about 5, 10, 15, 20, 25, 30, 35, 40, 50, 75, 100, or 150 consecutive amino acids thereof using any of the programs described above.

One skilled in the art can purify a polypeptide using standard techniques for protein purification to obtain an EIN6 polypeptide that is "substantially pure". As used herein, the term "substantially pure" refers to polypeptides which are substantially free of other proteins, lipids, carbohydrates or other materials with which it is naturally associated. The EIN6 proteins can be analyzed by standard SDS-PAGE and/or immunoprecipitation analysis and/or Western blot analysis, for example. The purity of an EIN6 polypeptide can also be determined by amino-terminal amino acid sequence analysis.

EIN6 Antibodies

The invention also provides antibodies immunoreactive with any EIN6 polypeptide, or antigenic fragments thereof, where an antibody may consist essentially of pooled monoclonal antibodies with different epitopic specificities, as well as distinct monoclonal antibody preparations is provided. Monoclonal antibodies are made from antigen containing fragments of the protein by methods well known to those skilled in the art (Kohler, et al., *Nature*, 256:495, 1975).

The term "antibody" as used in this invention includes intact molecules as well as fragments thereof, such as Fab, F(ab')2, and Fv capable of binding to an epitopic determinant present in EIN6 polypeptide. Such antibody fragments retain some ability to selectively bind with its antigen or receptor.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" refers to an antigenic determinant on an antigen to which the paratope of an antibody binds. Epitopic determinants often consist of chemically active surface groupings of molecules such as amino acids or sugar side chains and usually have specific three dimensional structural characteristics, as well as specific charge characteristics.

Antibodies which bind to the EIN6 polypeptide of the invention can be prepared using an intact polypeptide or fragments containing small peptides of interest as the immunizing antigen. For example, it may be desirable to produce antibodies that specifically bind to the N- or C-terminal domains of EIN6. The polypeptide or peptide used to immunize an animal may be derived from translated cDNA or may be chemically synthesized, and may further be conjugated to a carrier protein, if desired. Commonly used carriers which are chemically coupled to an immunizing peptide include keyhole limpet hemocyanin (KLH), thyroglobulin, bovine serum albumin (BSA), and tetanus toxoid.

Polyclonal or monoclonal antibodies can be further purified, for example, by binding to and eluting from a matrix to which the polypeptide or a peptide to which the antibodies were raised is bound. Those of skill in the art are familiar with various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

A cDNA expression library such as lambda gt11, can be screened indirectly for EIN6 peptides using antibodies specific for EIN6 epitopes. Such antibodies may be polyclonally or nionoclonally derived, and may be used to detect expression product indicative of the presence of EIN6 cDNA.

Plants with EIN6 Gene Mutations

Another embodiment of the invention relates to plants that have been altered to be insensitive to ethylene in their root. Such modifications include transgenic plants with decreased response to ethylene due to transformation with constructs using antisense or cosuppression technology that affect transcription or expression from the EIN6 gene. Such plants exhibit well-known ethylene insensitive phenotypes, such as delayed ripening, flowering, delayed senescence, browning, and altered sensitivity to pathogens.

Another embodiment of the invention relates to plants that have been altered to be insensitive to ethylene throughout the plant. Such modifications include transgenic plants with decreased response to ethylene due to transformation with constructs using antisense or cosuppression technology that affect transcription or expression from the EIN6 gene and the een gene. Such plants exhibit well-known ethylene insensitive phenotypes, such as delayed ripening, flowering, delayed senescence, browning, and altered sensitivity to pathogens.

In another embodiment, embodiments of the invention provide a method for producing a genetically modified plant characterized as having an altered ethylene-dependent phenotype as compared to a plant which has not been genetically modified (e.g., a wild-type plant). The method includes the steps of contacting a plant cell with at least one vector containing at least one nucleic acid sequence encoding an EIN6 gene or a mutant, homolog or fragment thereof, wherein the nucleic acid sequence is operably associated with a promoter, to obtain a transformed plant cell; producing a plant from the transformed plant cell; and thereafter selecting a plant exhibiting an altered ethylene-dependent phenotype.

Transgenic plants that result in an altered ethylene-dependent phenotype may be obtained by reduced expression of the EIN6 gene, or the EIN6 gene and the een gene. Thus, one embodiment of the invention includes plants transformed with antisense polynucleotides complementary to the EIN6 gene or fragments thereof wherein production of the antisense polynucleotides results in reduced expression of the EIN6 gene. In an alternate embodiment, reduced expression of EIN6 may also be achieved by methods such as cosuppression (Hooper, C. (1991) J. NIH Res. 3: 49–54) by operatively linking a truncated form of an EIN6 gene to a promoter. In an alternate embodiment, transgenic plants overexpressing the EIN6 gene are described. Such plants might be expected to display accelerated ripening and enhanced sensitivity to pathogens.

The term "genetic modification" as used herein refers to the introduction of one or more heterologous nucleic acid sequences, e.g., an EIN6 or an ein6 mutant encoding sequence, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, etc.

The term "exogenous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In one embodiment, at least one nucleic acid sequence encoding EIN6 or a variant thereof is operably linked with a promoter. It may be desirable to introduce more than one copy of an EIN6 polynucleotide into a plant for enhanced expression. For example, multiple copies of the gene would have the effect of increasing production of the EIN6 gene product in the plant.

Genetically modified plants of the present invention are produced by contacting a plant cell with a vector including at least one nucleic acid sequence encoding a EIN6 or a variant thereof. Suitable methods for the creation of such modified plants are found in Examples 8–10. To be effective once introduced into plant cells, the EIN6 nucleic acid sequence are operably associated with a promoter which is effective in the plant cells to cause transcription of EIN6. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non-transformed cells in culture, as described herein.

In embodiments of the invention, EIN6 and/or EEN expression is lowered in a plant by genetic transformation methods. Any method to downregulate EIN6 and/or EEN gene expression may be used, but typical examples include antisense technology, cosuppression, RNA inhibition (RNAi), and ribozyme inhibition. In the antisense method, for example, antisense molecules are introduced into cells that contain EIN6 and/or EEN, for example, and may function by decreasing the amount of EIN6 and/or EEN polypeptide production in a cell, or may function by a different mechanism. Antisense polynucleotides useful for the present invention are complementary to specific regions of a corresponding target mRNA. An antisense polynucleotide can be introduced to a cell by introducing an expressible construct containing a nucleic acid segment that codes for the polynucleotide. Antisense polynucleotides in context of the present invention may include short sequences of nucleic acid known as oligonucleotides, usually 10–50 bases in length, as well as longer sequences of nucleic acid that may exceed the length of the gene sequence itself.

Small Molecules

Accordingly, embodiments of the invention include methods of screening or identifying proteins, small molecules or other compounds which are capable of inducing or inhibiting the expression of the EIN6 genes and proteins. The assays may be performed in vitro using transformed or non-transformed cells, immortalized cell lines, or in vivo using transformed plant models enabled herein. In particular, the assays may detect the presence of increased or decreased expression of EIN6 (from *Arabidopsis* or other plants) genes or proteins on the basis of increased or decreased mRNA expression, increased or decreased levels of EIN6 protein products, or increased or decreased levels of expression of a marker gene (e.g., beta-galactosidase, beta-glucuronidase, green fluorescent protein, alkaline phosphatase or luciferase) operably joined to an EIN6 5' regulatory region in a recombinant construct. Cells known to express a particular EIN6, or transformed to express a particular EIN6, are incubated and one or more test compounds are added to the medium. After allowing a sufficient period of time (e.g., 0–72 hours) for the compound to induce or inhibit the expression of EIN6, any change in levels of expression from an established baseline may be detected using any of the techniques described above Other embodiments of the invention include methods for identifying proteins and other compounds which bind to, or otherwise directly interact with, the EIN6. The proteins and compounds include endogenous cellular components which interact with EIN6 in vivo and which, therefore, provide new targets for agricultural products, as well as recombinant, synthetic and otherwise exogenous compounds which may have EIN6 binding capacity and, therefore, are candidates for inhibition of the plant's response to ethylene. Thus, High Throughput Screening-derived proteins, DNA chip arrays, cell lysates or tissue homogenates may be screened for proteins or other compounds which bind to one of the normal or mutant EIN6 genes. Alternatively, any of a variety of exogenous compounds, both naturally occurring and/or synthetic (e.g., libraries of small molecules or peptides), may be screened for EIN6 binding capacity.

Accordingly, assays can be conducted to detect binding between EIN6 and another moiety. The EIN6 in these assays may be any polypeptide comprising or derived from a normal or mutant EIN6 protein, including functional domains or antigenic determinants of EIN6. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of EIN6 components and bound proteins or other compounds by immunoprecipitation; (3) BIAcore analysis; and (4) the yeast two-hybrid systems.

Embodiments of the invention also include methods of identifying proteins, small molecules and other compounds capable of modulating the activity of normal or mutant EIN6. Using normal cells or plants, the transformed cells and plant models of the present invention, or cells obtained from subjects bearing normal or mutant EIN6 genes, the present invention provides methods of identifying such compounds on the basis of their ability to affect the expression of EIN6, the activity of EIN6, the activity of other EIN6-regulated genes, the activity of proteins that interact with normal or mutant EIN6 proteins, the intracellular localization of the EIN6, changes in transcription activity, the presence or levels of membrane bound EIN6, or other biochemical, histological, or physiological markers which distinguish cells bearing normal and modulated EIN6 activity in plants.

In accordance with another aspect of the invention, the proteins described herein can be used as starting points for rational chemical design to provide ligands or other types of small chemical molecules. Alternatively, small molecules or other compounds identified by the above-described screening assays may serve as "lead compounds" in design of modulators of the ethylene response in plants.

Host Cells and Vectors

DNA sequences encoding EIN6 can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

As part of the present invention, the EIN6 polynucleotide sequences may be inserted into a recombinant expression vector. The terms "recombinant expression vector" or "expression vector" refer to a plasmid, virus or other vehicle known in the art that has been manipulated by insertion or incorporation of the EIN6 genetic sequence. Such expression vectors contain a promoter sequence which facilitates the efficient transcription of the inserted EIN6 sequence. The expression vector typically contains an origin of replication, a promoter, as well as specific genes which allow phenotypic selection of the transformed cells.

Methods which are well known to those skilled in the art can be used to construct expression vectors containing the EIN6 coding sequence and appropriate transcriptional/translational control signals. These methods include in vitro recombinant DNA techniques, synthetic techniques, and in vivo recombination/genetic techniques.

A variety of host-expression vector systems may be utilized to express the EIN6 coding sequence. These include but are not limited to microorganisms such as bacteria transformed with recombinant bacteriophage DNA, plasmid DNA or cosmid DNA expression vectors containing the EIN6 coding sequence; yeast transformed with recombinant yeast expression vectors containing the EIN6 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the EIN6 coding sequence; insect cell systems infected with recombinant virus expression vectors (e.g., baculovirus) containing the EIN6 coding sequence; or animal cell systems infected with recombinant virus expression vectors (e.g., retroviruses, adenovirus, vaccinia virus) containing the EIN6 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). For example, when cloning in bacterial systems, inducible promoters such as pL of bacteriophage gamma., plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted EIN6 coding sequence.

The EIN6 proteins produced by the method described above may be used, for example, for structural characterization studies, protein-protein interaction studies, protein-nucleic acid interaction studies, and the like. Isolation and purification of recombinantly expressed polypeptide, or fragments thereof, may be carried out by conventional means including preparative chromatography and immunological separations involving monoclonal or polyclonal antibodies.

Vector(s) employed in the present invention for transformation of a plant cell include a nucleic acid sequence encoding EIN6, operably linked to a promoter. To commence a transformation process in accordance with the present invention, it is first necessary to construct a suitable vector and properly introduce it into the plant cell. Details of the construction of vectors utilized herein are known to those skilled in the art of plant genetic engineering.

The term "operably linked" refers to functional linkage between a promoter sequence and a nucleic acid sequence regulated by the promoter. The operably linked promoter controls the expression of the nucleic acid sequence.

Promoters

The expression of structural genes may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., Nature, 310:511, 1984; Odell, et al., Nature, 313:810, 1985); the full-length transcript promoter from Figwort Mosaic Virus (FMV) (Gowda, et al., J. Cell Biochem., 13D: 301, 1989) and the coat protein promoter to TMV (Takamatsu, et al., EMBO J. 6:307, 1987). Alternatively, plant promoters such as the light-inducible promoter from the small subunit of ribulose bis-phosphate carboxylase (ssRUBISCO) (Coruzzi, et al., EMBO J., 3:1671, 1984; Broglie, et al., Science, 224:838, 1984); mannopine synthase promoter (Velten, et al., EMBO J., 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., Mol. Cell. Biol., 6:559, 1986; Severin, et al., Plant Mol. Biol., 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., Proc. Natl. Acad. Sci., U.S.A., 90:4567, 1993); In2-1 and In2-2 regulator sequences which are activated by substituted benzenesulfonamides, e.g., herbicide safeners (Hershey, et al., Plant Mol. Biol., 17:679, 1991); and the GRE regulatory sequences which are induced by glucocorticoids (Schena, et al., Proc. Natl. Acad. Sci., U.S.A., 88:10421, 1991). Other promoters, both constitutive and inducible will be known to those of skill in the art.

The particular promoter selected should be capable of causing sufficient expression to result in the production of an effective amount of structural gene product to alter an ethylene-dependent phenotype. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al., Plant J., 2:291, 1992). Other tissue specific promoters useful in transgenic plants, including the cdc2a promoter and cyc07 promoter, will be known to those of skill in the art. (See for example, Ito, et al., Plant Mol. Biol., 24:863, 1994; Martinez, et al., Proc. Natl. Acad. Sci. USA, 89:7360, 1992; Medford, et al., Plant Cell, 3:359, 1991; Terada, et al., Plant Journal, 3:241, 1993; Wissenbach, et al., Plant Journal, 4:411, 1993).

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthine-guanine phospho-ribosyltransferase and amino-glycoside 3'-O-phospho-transferase II (kanamycin, neomycin and G418 resistance). Other suitable markers will be known to those of skill in the art.

Methods of Transforming Plants

EIN6 and/or EEN nucleic acid sequences utilized in the present invention can be introduced into plant cells using Ti plasmids of *Agrobacterium tumefaciens*, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., Science, 227:1229, 1985, both incorporated herein by reference). In addition to plant transformation vectors derived from the Ti or root-inducing (Ri) plasmids of *Agrobacterium*, alternative methods may involve, for example, the use of liposomes, electroporation, chemicals that increase free DNA uptake, transformation using viruses or pollen and the use of microprojection.

One of skill in the art will be able to select an appropriate vector for introducing the EIN6 and/or EEN nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of an EIN6 and/or EEN gene, or a mutant form of the EIN6 and/or EEN gene.

For example, an EIN6 and/or EEN nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, Biotechnology, 1: 262, 1983; Hoekema, et al., Nature, 303:179, 1983). Such a binary system is preferred because it does not require integration into the Ti plasmid of *Agrobacterium*, which is an older methodology.

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium;* or 3) transformation of seeds, apices or meristems with *Agrobacterium*. In addition, gene transfer can be accomplished by in planta transformation by *Agrobacterium*, as described by Bechtold, et al., (C. R. Acad. Sci. Paris, 316:1194, 1993). This approach is based on the vacuum infiltration of a suspension of *Agrobacterium* cells.

One method of introducing EIN6 and/or EEN nucleic acid sequences into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, EIN6 and/or EEN nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

EIN6 and/or EEN nucleic acid sequences can also be introduced into plant cells by electroporation (Fromm, et al., Proc. Natl. Acad. Sci., U.S.A., 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing EIN6 and/or EEN nucleic acid into a plant cell is high velocity ballistic penetration by small particles with the nucleic acid to be introduced contained either within the matrix of such particles, or on the surface thereof (Klein, et al., Nature 327:70, 1987). Bombardment transformation methods are also described in Sanford, et al. (Techniques 3:3–16, 1991) and Klein, et al. (Bio/Techniques 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing EIN6 and/or EEN into the plant cell, including chemical and physical means as described above. Preferably, contacting refers to introducing the nucleic acid or vector into plant cells (including an explant, a meristem or a seed), via *Agrobacterium tumefaciens* transformed with the EIN6 and/or EEN nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see Methods in Enzymology, Vol. 118 and Klee, et al., Annual Review of Plant Physiology, 38:467, 1987). Utilizing the leaf disk-transformation-regeneration method of Horsch, et al., Science, 227:1229, 1985, disks are cultured on selective media, followed by shoot formation in about 2–4 weeks. Shoots that develop are excised from call and transplanted to appropriate root-inducing selective medium. Rooted plantlets are transplanted to soil-as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that exhibit an altered response to ethylene.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting an altered ethylene-dependent phenotype as compared with wild-type plants can be selected by visual observation. For example, an altered ethylene-dependent phenotype may be detected by utilization of the "triple response." The "triple response" consists of three distinct morphological changes in dark-grown seedlings upon exposure to ethylene: inhibition of hypocotyl and root elongation, radial swelling of the stem and exaggeration of the apical hook. Thus, a triple response displayed in the presence of ethylene inhibitors would indicate one type of altered ethylene-dependent phenotype. Altered responses to ethylene may be visualized by other methods in addition to the "triple response" phenotype. For example, since ethylene affects a wide group of other plant characteristics, such as flowering, fruit ripening, and senescence, one of skill in the art would be able to design other types of visual screens for altered responses to ethylene, depending on the plant species being tested. Types of screens that could be designed include, for example, screens for delayed leaf or flower senescence or delayed fruit ripening in response to ethylene application.

In some embodiments of the invention, ethylene gas may be used to analyze ethylene response phenotypes. Additionally, molecules which are precursors to ethylene may be used. For example, the endogenous ethylene precursor ACC may be provided to the plant to examine the response to ethylene. Once taken up by the plant, the ACC is converted to ethylene by natural plant processes. Alternatively, synthetic compounds which degrade to produce ethylene may be sprayed on the surface of the plant. For example, ethephon (chloro-ethanephosphonic acid), is a commercially available compound that is typically sprayed on the surface of the plant, liberating ethylene once inside the plant tissue. Therefore, ethylene, ethylene analogs, or ethylene generating agents may be useful to screen and analyze ethylene response phenotypes according to the present invention.

Several commercially available herbicides, such as Arvest, Bromeflor, Flordimex, Etherel, etc., may contain ethephon (chloro-ethanephosphonic acid) as an active ingredient. Weed growth can be slowed or stopped by the application of these herbicides because the ethylene that is liberated acts as a plant growth regulator, to slow or stop growth. Accordingly, embodiments of the present invention may include ethylene insensitive mutant or transgenic plants that are herbicide resistant or herbicide insensitive due to the altered levels of functional EIN6 and/or EEN present in these plants.

The role of ethylene in the reduction of hypocotyl and root elongation has not yet been elucidated. One possibility relates to the theory that cortical microtubules associated with the plasma membrane may direct the cellulose synthase complex that is responsible for cell wall deposition. The drug taxol acts to stabilize microtubules by inhibiting microtubule depolymerization (Schiff and Horwitz 1981) and may inhibit the shift in cortical microtubules upon ethylene treatment,(Heinstein and Chang 1994). To determine if taxol could affect the ethylene insensitivity phenotype of ein6/een mutants, wild-type and ein6/een mutants were given a 10 day taxol treatment in the dark (Example 12). Interestingly, the ein6/een mutants were found to be especially sensitive to even low levels (0.1 μM) of taxol. The mutants treated with taxol had a phenotype approaching that of the wild-type seedlings.

Accordingly, another embodiment of the invention is a mutant or transgenic plant with altered ethylene sensitivity and taxol hypersensitivity is disclosed. The taxol hypersensitivity phenotype may be useful, for example, in assays to examine microtubule action or cytoskeletal activity, particularly in relation to cell elongation. One method of creating a plant with a taxol hypersensitivity would involve transforming a plant with an antisense construct of both the EIN6 and the EEN genes.

Ethylene affects a vast array of agriculturally important plant processes, including fruit ripening, flower and leaf senescence and leaf abscission, in addition to the readily observable "triple response" of seedlings. For example, plants having a decreased sensitivity to ethylene may have better storage characteristics. Fruits of such plants may ripen more slowly. This could be an advantage for post-harvest handling of agricultural products, such as processing, packaging, and storage of fruit. There may be less of a loss of fruit crops due to such traditionally damaging problems as rotting, over-ripening, and degradation. It may be possible to better control the ripening rate and ripening characteristics of plants carrying these modified EIN6 and/or EEN genes. It is possible, as well, to link the modified genes to specific promoters in order to better modulate the expression of the genes so that the response to ethylene is turned off at certain times or in certain tissues, while acting normally in other parts of the plant or at other times in development.

Plants having reduced EIN6 and/or EEN activity and thus a reduced sensitivity to ethylene to could be useful for the floral industry. Since ethylene may be involved in floral senescence, these modified plants may have a longer flower longevity. Further, it may be useful to use the present invention to create vegetative crops that do not bolt or flower easily. For example, lettuce, spinach, other leafy vegetables, or certain herbs may have higher yields due to decreased floral initiation. Because ethylene has been implicated in senescence, potted plants made according to the present invention may last longer than control plants due to reduced leaf senescence.

One of skill in the art would appreciate that different plants or different agricultural crops may benefit from different types of promoter/EIN6 and or promoter/EEN gene modifications. For example, in some plants it may be desirable to be able to decrease the sensitivity constitutively using, for example, a CaMV35S promoter linked to the modified EIN6 gene. Other plants may benefit from decreasing the sensitivity to ethylene only at fruit ripening, for example, by linking the modified EIN6 gene to a fruit ripening-specific promoter. It may be useful to create plants that have modified ethylene sensitivity only in the vegetative parts of the plant. In another example, it may be useful to prepare plants having a modified EIN6 and/or EEN gene so that the ethylene sensitivity is decreased only at high temperatures. Such a scenario may be important in post-harvest storage and transportation of fruit, for example. It may be useful to link the gene to a promoter such that the ethylene insensitivity characteristic is brought about only when the plant is stored in the darkness by operably linking a darkness-inducible promoter to the modified modified EIN6 and/or EEN gene. This may be particularly useful for managing long term storage of certain crops between the time of harvest and the time of display for sale. Once the agricultural product is unpacked for market display in the light, for example, the modified EIN6 and/or EEN gene gene would be downregulated, the ethylene insensitivity would decrease, and ripening would resume. Many other options for modifying specific crops as desired can be designed by one of skill in the art Alternatively, it may be of interest to produce plants that overexpress one or more members of the EIN6 gene family. This may cause plants to have increased sensitivity to ethylene, or it may create other desirable plant phenotypes which may be of agronomic importance. The EIN6 overexpression may be either constitutive, inducible, or tissue-specific.

Further, it may be of interest to produce plants that overexpress one or more members of the EEN gene family. This may cause plants to have increased sensitivity to ethylene, or it may create other desirable plant phenotypes which may be of agronomic importance. The EEN overexpression may be either constitutive, inducible, or tissue-specific.

Further, since ethylene pathways involve the action of many gene products, as detailed herein, it may be useful to engineer plants having modified EIN6 and/or EEN genes in combination with other modified genes in the ethylene synthesis or response pathway. The other ethylene pathway genes may be inactivated or partially inactivated, for example, by insertional mutation, or point mutation, by antisense technology, or by molecular decoy technology. Alternatively, the other ethylene pathway genes may be conditionally overexpressed or may be preferentially expressed (such as in certain tissues, or in response to certain developmental or environmental cues).

As describe herein, ethylene signaling processes may interact with the signaling processes of other hormones, such as auxin. Therefore, mutant or transgenic plants having altered expression of EIN6 and/or EEN genes may exhibit useful alterations in auxin-related pathways. Further, since ethylene is released upon certain types of pathogen infection, mutant or transformed plants having an altered ethylene sensitivity may be useful to modify responses to pathogens. In fact, since many genes have altered expression characteristics in response to ethylene application, mutant or transgenic plants carrying altered EIN6 and/or EEN genes to alter the sensitivity may be useful in altering a myriad of physiological roles and morphological phenotypes in plants.

The ability to control the sensitivity of plants to ethylene could thus significantly improve the quality and longevity of many crops. The invention includes plants produced by the method of the invention, as well as plant tissue and seeds.

In yet another embodiment, the invention provides a method for producing a genetically modified plant cell such that a plant produced from said cell has an altered ethylene-dependent phenotype compared with a wild-type plant. The method includes contacting the plant cell with an EIN6 and/or EEN nucleic acid sequence to obtain a transformed plant cell; growing the transformed plant cell under plant forming conditions to obtain a plant having an altered ethylene-dependent phenotype. Conditions such as environmental and promoter inducing conditions vary from species to species, but should be the same within a species.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

EXAMPLE 1

Mapping of the Ein6 Locus

The EIN6 gene was isolated from a population of fast neutron-mutagenized plants, and was originally mapped to the bottom of chromosome 3, 17.6 cM north of ngal 12 (Roman, G. et al. (1995) "Genetic analysis of ethylene signal transduction in *Arabidopsis thaliana:* five novel mutant loci integrated into a stress response pathway" Genetics 139(3): 1393–1409). Further mapping indicated that the gene was located farther north, located in a ~12 cM interval between the markers TOPP5 and g19397 (FIG. 2). The acetolactate synthase gene is located in this interval, and was used to screen bacterial artificial chromosome (BAC) libraries to identify BAC clones in this region. Additional markers were developed from cloned genes in the region and BAC end sequences obtained from TAIL-PCR clones and the *Arabidopsis* Genome Initiative.

Using these markers, EIN6 was mapped on an F2 population of 496 plants. It was found that the closest flanking marker to the north, F1K9-T7, resided on the BAC T29H11 (Accession AL049659), which was sequenced by the ESSA sequencing consortium. The lone plant recombinant at the closest flanking marker to the south of the gene, F11N9, remained recombinant at a marker made from the southern end of the BAC (29H11-End), indicating that the genomic sequence of EIN6 was located on T29H11 (FIG. 2). The genomic sequence in this 71 kb interval was exploited to design a series of markers that allowed the EIN6 locus to be fine mapped to a 44 kb region between the markers 12.1 and 29H11-End (FIG. 1).

EXAMPLE 2

Identification of the Ein/6 Mutation

Although the ein6 mutation was induced by fast neutrons, no evidence of a deletion was observed when genomic Southern blots of the mutant were probed with F3E7, a BAC that overlapped this region (data not shown). Using the genomic data available, a novel approach was undertaken to identify the mutation in the EIN6 gene. Denaturing High Performance Liquid Chromatography (DHPLC) is a technique that is capable of identifying single base mismatches in double stranded DNA (O'Donovan, 1998). Primers were designed to amplify overlapping ~500 bp PCR fragments that covered the 44 kb interval between the two closest recombinant markers. PCR fragments that contain no mismatches elute from the DHPLC column as single peaks. In the event that a mismatch is present in a particular fragment, multiple peaks are observed. Multiple peaks were only observed for a single fragment contained within the interval. Sequencing of this fragment from both wild type and mutant plants identified a 7 base deletion in the putative coding region of T29H11.50, a gene that had been predicted by annotation (FIG. 2). This 7 base pair deletion (indicated by asterisks in FIG. 2) causes a frame shift and introduces a stop codon into the coding sequence. There is one homolog of EIN6 in the *Arabidopsis* genome, which shares 53% identity with the overall putative protein sequence. It is annotated as a gene of unknown function and is located on chromosome 5.

EXAMPLE 3

The Original Ein6 Mutation is Two Genes

The original mutation ein6 had been characterized as a recessive mutant, which conferred, reduced fertility. Backcrosses of ein6 mutant plants to the parental line Lansberg Erecta (Ler) yielded interesting results. Upon careful analysis of the F2 seedlings grown in an ethylene precursor, three phenotypes were seen. Two were those that had been seen before, wild type and ethylene insensitive (ein-like). The third was a weak ethylene insensitive phenotype, with only an ethylene insensitive root (eir-like). The numbers of each class were counted in the F2 population. They corresponded to the following ratio: 12:3:1, with 12/16 of the plants being of the wild type (triple response) phenotype, 3/16 of the plants being of the eir (ethylene insensitive root) phenotype, and 1/16 of the plants being ein (ethylene insensitive) phenotype. Each of these classes were genotyped for the ein6 mutation. All of the ein-like and eir-like plants turned out to have the ein6 mutation. This indicates that the original mutation is actually two recessive genes, one conferring the eir phenotype, and the other not having a visible phenotype as a seedling.

EXAMPLE 4

Complementation with an EIN6 Genomic Fragment Rescues the Ein6/Een Phenotype

*Agrobacterium* transformation was used to transform *Arabidopsis* double mutant ein6/een plants. These were transformed with a 6.2 kb genomic fragment containing EIN6 plus 0.9 kb of its promotor. The plants were tested for kanamycin resistance in the T1 generation. The T2 generation of the kanamycin resistant plants was plated on media containing a precursor to ethylene to see if they would have an ethylene sensitive or insensitive phenotype. All of the transformed lines showed sensitivity to ethylene, some even displaying a complete triple response. A control experiment which only transformed *Arabidopsis* with a vector without any EIN6 genomic DNA, showed ethylene insensitivity, like the parental plants. This experiment demonstrated that the ein6/een double mutant could be made sensitive to ethylene by transformation with the EIN6 genomic DNA.

EXAMPLE 5

Isolation and Characterization of the Ein6 Gene

Annotation predicted that T29H11.50 genomic clone would encode a ~4.5 kb cDNA, so the fragment containing the ein6 mutation was used to probe a size selected Col-0 cDNA library to isolate the gene. A single clone was identified out of more than 300,000 plaques, and contained a partial cDNA of 3.4 kb. The 5' end of the cDNA was isolated by direct PCR from the cDNA library, and the two fragments were ligated to yield a cDNA of 4580 bp.

Because the ein6 mutation was generated in a different ecotype, the genomic sequence of the EIN6 locus in the L(er) ecotype was determined. The L(er) genomic sequence differed from the Col-0 sequence only slightly, lacking two nucleotides in the 5' unitranslated region, changing a single nucleotide at a wobble base that did not alter the identity of the encoded amino acid, and a three base in-frame deletion that eliminated a single residue from a stretch of glutamic acids near the carboxyl terminus of the predicted polypeptide. Based on the sequence of the Col-0 cDNA, the intron-exon boundaries were determined for the EIN6 locus in L(er), yielding a cDNA of 4575 bp (SEQ ID NO: 22).

The EIN6 cDNA encodes a protein of 1359 amino acids with a predicted molecular weight of 152.5 kDa (FIG. 3; SEQ ID NO: 20). Without being bound by any theory, the deduced amino acid sequence provides some indications of function. The most striking structural feature is the presence of three complete zinc fingers at the extreme carboxyl terminus of the polypeptide. The fingers fall into the GLI1 class of DNA-binding $C_2H_2$ zinc fingers (FIG. 5).

Interestingly, an incomplete fourth zinc finger is located adjacent to the three complete fingers, but lacks the second histidine required for zinc coordination (FIG. 3). Without intending to be bound by any theory, a potential role for EIN6 in DNA binding is supported by the presence of four putative nuclear localization signals in the carboxyl half of the protein (FIG. 3). Moreover, the presence of two acidic stretches of aspartic acid and glutamic acid adjacent to the zinc fingers (FIG. 3) is reminiscent of eukaryotic transcriptional activators.

The amino terminal portion of the EIN6 protein bears significant homology to the retinoblastoma binding protein 2 (RBP2; FIG. 6). RBP2 was isolated based on its ability to interact with the retinoblastoma (RB) tumor suppressor in in vitro assays (Defeo-Jones, 1991). The similarity to RBP2 is found over an approximately 350 residue stretch that does not contain the motifs that are known to be required for interaction between RBP2 and RB (Kim, 1994). Interestingly, homologous proteins fall into two distinct classes. The first class contains RBP2, and is characterized by approximately 50% identity over a 40 amino acid region at the amino terminus of EIN6, a gap, and 35% identity and 50% similarity over approximately 250 residues. The non-homologous stretch between these two domains is comprised of 60 amino acids in EIN6, and more than 300 amino acids in its homologs. The second class of homologous proteins are similar over the entire stretch of the first 350 amino acids at the amino terminus of EIN6, possessing about 26% identity and 42% similarity. This class contains the yeast repressor of photolyase gene transcription, RPH1p (Jang, 1999), which is also homologous to EIN6 in the zinc finger domain.

Unlike RPH1p, EIN6 possesses an interval of more than 500 amino acids between the RBP2 homology domain and the carboxyl terminal zinc fingers. This region is not homologous to any protein in the database, but does contain two prominent structural features. Immediately following the RBP2 homology domain, a coiled coil motif is predicted, suggesting that EIN6 is capable of protein-protein interaction. In addition, an ATP/GTP binding P-loop is also predicted (FIG. 3).

While isolating 5' end clones by PCR directly from the cDNA library, clones lacking nucleotides 2220–2322 were obtained. Without being bound to any theory, these data suggest that the primary EIN6 transcript undergoes alternative splicing. Removal of this intron introduces a stop codon immediately after the last codon preceding the intron. Translation of this splice variant is predicted to yield a protein that possesses the complete RBP2 homology domain, but lacks the predicted coiled coil region and the zinc fingers (FIG. 4). The 7 bp deletion in the ein6 mutant introduces a frame shift approximately 75 nucleotides 5' of the alternatively-spliced intron, but the translated mutant protein still retains the RBP2 homology domain (data not shown). These data suggest that the form of EIN6 required for normal ethylene responses is the full length protein containing the coiled coil domain and zinc fingers.

EXAMPLE 6

Genetic Mapping of the Second Enhancer Mutation Een

The mapping of the second enhancer mutation een and the future cloning of the EEN gene is an important goal, in view of the fact that een is currently the only known enhancer in the ethylene pathway. Mapping of the second enhancer mutation (een) using twenty-six markers distributed evenly across the five chromosomes of the genome identified a new area of linkage in the ein6/een background to chromosome four. A small mapping population between the strains ein6/een in Landsberg and Columbia was generated to begin the mapping, with this population of only sixteen plants linkage was seen to markers nga1139 on chromosome four, and nga1107 on chromosome four. Using a larger population of 180 chromosomes four recombinants were seen with the marker nga1139, and no recombinants were seen with the marker nga1107. A large mapping population of ein6/een in the Landsberg background crossed to Nd-0 had been previously generated for the mapping of the ein6 mutation. This population is useful for fine mapping of the ein mutation. To date, 360 chromosomes from this cross have been analyzed for recombinants in this region. The een mutation has been narrowed to a region containing eight BACs at the end of chromosome four using SSLP markers.

EXAMPLE 7

Isolation of Other Ein6 Alleles to Assist in Characterization of the Role of EIN6 in the Ethylene Pathway Alleles of ein6 in the Columbia ecotype can be isolated so that EIN6 can be better classified in the ethylene signaling pathway. Currently four alleles have been isolated, from the Salk Institute Genomic Analysis Laboratory T-DNA collection (ein6-2 through ein6-5). These alleles do not display an obvious ethylene insensitive root like ein6-1 in Ler. Further analysis using homozygous insertional lines of these alleles can be performed to determine whether a difference exists between the Landsberg and Columbia ecotypes that may account for the lack of a noticeable phenotype.

EXAMPLE 8

Creation of Ethylene Insensitive Plants Using EIN6 Complementary DNA

As described in the paragraphs above, the ein6 mutant *Arabidopsis* plants were found to exhibit increased root insensitivity to ethylene, whereas the double mutant ein6/een plants exhibited increased whole plant insensitivity to ethylene. This finding can be of use, for example, in designing a strategy to create other plant species with altered root or whole plant ethylene sensitivity. For example, an EIN6 complementary DNA clone containing a section of the coding region is subcloned into a plant transformation vector. The plant transformation vector contains a cauliflower mosaic virus 35S promoter and a polyadenylation site to allow for expression of the gene in plants (Schardl, C. L. et al. (1987) "Design and construction of a versatile system for the expression of foreign genes in plants" Gene, 61:1–11). The plasmid is then introduced into *Agrobacterium tumefaciens* cells by electroporation, and the bacterial transformants are selected using a kanamycin selection marker. *Agrobacterium* cells carrying the EIN6 complementary DNA are then used to infect tomato plants by the leaf disk transformation method of Horsch et al (Science (1985) 227: 1229). The same plasmid, lacking the EIN6 DNA, is used as a control. Disks are cultured on media containing kanamycin, followed by shoot formation. The shoots are then transplanted to root-inducing selective medium. Rooted plantlets are transplanted to soil.

In order to study the effect of the EIN6 complementary DNA clone on the ethylene response in the transformed plants, transformed plantlets are examined for the presence of the ethylene-mediated triple response phenotype (Guzman and Ecker (1990) "Exploiting the triple response of *Arabidopsis* to identify ethylene-related mutants", Plant Cell 2, 513–523). Plantlets are grown in the dark for 3 days in the presence or absence of 10 µl of ethylene/liter of air. The number of plants displaying an ethylene insensitive phenotype is then determined. These plants are further selected and grown to maturity. Plants transformed with the EIN6 antisense construct are expected to have a ethylene insensitive root phenotype.

Following the above method, but transforming with both the EIN6 and EEN antisense constructs would also be possible. Plants transformed with antisense constructs of both genes would be expected to have an ethylene insensitive whole plant phenotype.

EXAMPLE 9

Overexpression of EIN6 in Plants

A plasmid is constructed to place EIN6 coding sequences downstream of the CaMv 35S promoter, to result in high level expression of EIN6 when transformed into tomato plants. The resulting plasmid is transformed into *Agrobacterium tumefaciens* as described in Example 8. *Agrobacterium* cells carrying the EIN6 coding sequence are used to transform tomato plants by the leaf disk method as described above. The same plasmid, lacking the EIN6 coding sequences, is used as a control.

The transformed plantlets are tested for an altered response to ethylene by exposure to air or ethylene as described in Example 8. Plants which display an increased sensitivity to ethylene, particularly in the root, are obtained.

EXAMPLE 10

Creation of Ethylene-Insensitive Plants Using Cosuppression

A truncated EIN6 DNA fragment corresponding to a section of the coding region is subcloned into a plant transformation vector. The plant transformation vector contains the cauliflower mosaic virus 35S promoter and a polyadenylation site to allow for expression of the gene in plants as described in Example 8. The plasmid is introduced into *Agrobacterium tumefaciens* cells by electroporation as described above, and the bacterial transformants are selected using a selection marker such as kanamycin. *Agrobacterium* cells carrying the EIN6 fragment are used to infect plants using the leaf disk method as described above. The same plasmid, lacking the EIN6 DNA, is used as a control.

The transformed plantlets are examined for the presence of the ethylene-mediated triple response phenotype as described above. Plantlets are grown in the dark for 3 days in the presence or absence of 10 µl of ethylene/liter of air. The number of plants displaying an ethylene-insensitive phenotype are determined. These plants are grown to maturity. Plant lines are obtained which display an insensitivity to ethylene, particularly in the root.

Alternatively, both a truncated EIN6 DNA and a truncated EEN DNA fragment may be subcloned into the vector, following the method described above. Plant lines obtained from a cosuppression of both EIN6 and EEN genes may be expected to display an insensitivity to ethylene and hypersensitivity to taxol application (see Example 12).

EXAMPLE 11

Determination of Epistasis and Isolation of Double Mutants

Analysis of gene function is greatly assisted by the creation of double mutants. Accordingly, ethylene pathway double mutants were utilized to further examine the role of EIN6 in the ethylene pathway. To prepare the double mutants, strains were backcrossed at least twice to remove potential background effects on the ethylene phenotype before double mutant construction. Chi-square analysis was performed on the $F_2$ segregation ratios to examine possible epistasis relationships. Double mutants then were isolated to demonstrate the genetic interaction between the mutant phenotypes.

For example, ctr1-3 ctr1-1, ein3-2 ctr1-1, ein5-1 ctr1-1, ein7 ctr1-1, eir2-1eir1-1ein3-1 eir1-1, ein5-1 eir1-2, ctr1-1 eir1-1, ctr1-1 aux1-21, ein2-1, ein2-1 eto 1-1, ein2-1 hls1-1 and eir1-1 aux1-21 double mutants were obtained by progeny testing $F_2$ plants of each parental mutant phenotype to find a plant of the genotype m1/m1, +m2; the double mutants were identified as seedlings with a new phenotype in the $F_3$ generation. The genotype of each double mutant was verified by failure to complement the hypostatic mutation. The einctr1-1 hls1-1, etol-1-1 hls1-1 and eir1-1 hls1-1 double mutants were identified in $F_2$ progenies as seedlings expressing both mutant phenotypes. The ctr1-5 allele was created by the insertion of a kanamycin-resistant marked T-DNA into the CTR1 gene (Kieber et al. 1993). This selectable marker was used to isolate recombinants between ein2-1 and ctr1-5. $F_2$ seeds from a ctr1-5 by ein2-1 cross were examined for ethylene insensitive seedlings in the presence of 50 µg/ml kanamycin. Kanamycin-resistant (kan$^r$) $F_2$ Ein$^-$ plants were progeny tested for the presence of both the kan$^r$ marker and Ein$^-$ phenotype. The double mutant was then verified by the failure to complement ctr1-1.

Following this method, plants having the single mutations ein6 or een can be crossed to form double mutations with any suitable ethylene pathway mutant, such as those listed above.

EXAMPLE 12

The Ethylene Insensitive Ein6/Een Double Mutants are Sensitive to Taxol

The double mutants ein6/een were found to be sensitive to the microtubule stabilizer taxol. Wild-type Landsberg seedlings or ein6/een mutant seedlings were grown in the presence of either 0 µM, 0.1 µM, or 1 µM taxol for 10 days in the dark, following the method of Roman and Ecker (Phil. Trans. R. Soc. Lond. B. 350: 75–81, 1995, which is herein incorporated by reference in its entirety). The main effect of the addition of 1 µM taxol on both wild-type and ein6/een mutant dark grown seedlings was an inhibition of elongation. Hypocotyl cells of the taxol-treated tissue appeared shorter and rounder than wild-type cells. The ein6/een mutant seedlings treated with 1 µM taxol were significantly shorter than non-treated ein6/een mutant seedlings, displaying a phenotype very similar to the wild-type seedlings treated with 1 µM taxol. The ein6/een mutant seedlings treated with only 0.1 µM taxol also showed a shortened phenotype, while the wild-type seedlings with the same level of taxol did not have an altered size as compared to untreated seedlings. From these observations, it has been concluded that the ein6/een double mutation, (or possibly the een single mutation) is responsible for the taxol sensitivity phenotype.

Because the ein6/een double mutants are hypersensitive to taxol, it may be desirable to create other plant species with this trait. This could be done, for example, by preparing plants that have reduced expression of both the EIN6 and the EEN gene, following the instructions in Examples 8 and 10, or using any method of reducing expression of a gene, such as antisense, cosuppression, RNA interference, molecular decoy methods, and the like.

While the present invention, including preferred embodiments, has been described fully and completely herein, it is to be understood that modifications will occur to those skilled in the art without departing from the spirit of the invention. The scope of the invention is therefore to be determined solely by the appended claims.

What is claimed is:

1. A plant cell comprising a recombinant polynucleotide encoding the amino acid sequence of SEQ ID NO: 20.

2. The plant cell of claim 1, wherein said plant cell is from a monocotyledonous plant.

3. The plant cell of claim 1, wherein said plant cell is from a dicotyledonous plant.

4. The plant cell of claim 1, wherein said plant cell is from a fruit.

5. The plant cell of claim 1, wherein said recombinant polynucleotide comprises SEQ ID NO: 22.

6. The plant cell of claim 1, wherein said recombinant polynucleotide is operably linked to a promoter.

7. The plant cell of claim 6, wherein said promoter is a constitutive promoter.

8. The plant cell of claim 6, wherein said promoter is a tissue-specific promoter.

9. The plant cell of claim 6, wherein said promoter is an inducible promoter.

* * * * *